(12) United States Patent
Tamarkin et al.

(10) Patent No.: US 10,967,063 B2
(45) Date of Patent: Apr. 6, 2021

(54) SURFACTANT-FREE, WATER-FREE FORMABLE COMPOSITION AND BREAKABLE FOAMS AND THEIR USES

(71) Applicant: Vyne Pharmaceuticals Ltd., Rehovot (IL)

(72) Inventors: Dov Tamarkin, Ness Ziona (IL); Elana Gazal, Rehovot (IL); Irakliy Papiashvili, Ashkelon (IL); Yohan Hazot, Rehovot (IL); David Schuz, Gimzu (IL); Rita Keynan, Rehovot (IL)

(73) Assignee: Vyne Therapeutics Inc., Bridgewater, NJ (US)

( * ) Notice: Subject to any disclaimer, the term of this patent is extended or adjusted under 35 U.S.C. 154(b) by 0 days.

(21) Appl. No.: 16/019,623

(22) Filed: Jun. 27, 2018

(65) Prior Publication Data
US 2019/0000980 A1    Jan. 3, 2019

Related U.S. Application Data

(62) Division of application No. 13/499,709, filed as application No. PCT/IB2010/002613 on Oct. 1, 2010, now Pat. No. 10,029,013.

(60) Provisional application No. 61/248,144, filed on Oct. 2, 2009, provisional application No. 61/322,148, filed on Apr. 8, 2010, provisional application No. 61/331,126, filed on May 4, 2010, provisional application No. 61/349,911, filed on May 31, 2010, provisional application No. 61/380,568, filed on Sep. 7, 2010, provisional application No. 61/385,385, filed on Sep. 22, 2010, provisional application No. 61/388,884, filed on Oct. 1, 2010.

(51) Int. Cl.
| | | |
|---|---|---|
| A61K 47/44 | (2017.01) | |
| A61K 47/06 | (2006.01) | |
| A61K 9/00 | (2006.01) | |
| A61K 9/12 | (2006.01) | |
| A61K 47/24 | (2006.01) | |
| A61K 45/06 | (2006.01) | |
| A61K 47/10 | (2017.01) | |
| A61K 8/36 | (2006.01) | |
| A61K 8/34 | (2006.01) | |
| A61Q 19/10 | (2006.01) | |
| A61Q 19/00 | (2006.01) | |
| A61Q 17/04 | (2006.01) | |
| A61K 8/31 | (2006.01) | |
| A61K 47/02 | (2006.01) | |
| A61K 31/192 | (2006.01) | |
| A61K 31/137 | (2006.01) | |
| A61K 47/12 | (2006.01) | |
| A61K 31/593 | (2006.01) | |
| A61K 31/573 | (2006.01) | |
| A61K 31/57 | (2006.01) | |
| A61K 31/4164 | (2006.01) | |
| A61K 31/65 | (2006.01) | |

(52) U.S. Cl.
CPC .............. *A61K 47/44* (2013.01); *A61K 8/31* (2013.01); *A61K 8/342* (2013.01); *A61K 8/361* (2013.01); *A61K 9/0014* (2013.01); *A61K 9/0048* (2013.01); *A61K 9/12* (2013.01); *A61K 9/122* (2013.01); *A61K 9/124* (2013.01); *A61K 31/137* (2013.01); *A61K 31/192* (2013.01); *A61K 31/4164* (2013.01); *A61K 31/57* (2013.01); *A61K 31/573* (2013.01); *A61K 31/593* (2013.01); *A61K 31/65* (2013.01); *A61K 45/06* (2013.01); *A61K 47/02* (2013.01); *A61K 47/06* (2013.01); *A61K 47/10* (2013.01); *A61K 47/12* (2013.01); *A61K 47/24* (2013.01); *A61Q 17/04* (2013.01); *A61Q 19/00* (2013.01); *A61Q 19/10* (2013.01); *A61K 2800/31* (2013.01); *A61K 2800/33* (2013.01)

(58) Field of Classification Search
None
See application file for complete search history.

(56) References Cited

U.S. PATENT DOCUMENTS

| 1,159,250 A | 11/1915 | Moulton |
| 1,666,684 A | 4/1928 | Carstens |
| 1,924,972 A | 8/1933 | Beckert |
| (Continued) | | |

FOREIGN PATENT DOCUMENTS

| AU | 198780257 A | 9/1986 |
| AU | 782515 B2 | 12/2005 |
| (Continued) | | |

OTHER PUBLICATIONS

"Everything but the Olive." The Olive Oil Source 1998-2016 [online]. Retrieved from the Internet: http://www.oliveoilsource.com/pageA chemical-characteristics.

(Continued)

*Primary Examiner* — Patricia Duffy
*Assistant Examiner* — Garen Gotfredson
(74) *Attorney, Agent, or Firm* — Finnegan, Henderson, Farabow, Garrett & Dunner, LLP

(57) ABSTRACT

A substantially surface active agent-free and foam adjuvant-free composition which includes a hydrophobic solvent, a wax and a propellant. A substantially surface active agent-free and foam adjuvant-free composition, further comprising, a tetracycline antibiotic, or one or more other active agents. A method of treatment, using a substantially surface active agent-free and substantially foam adjuvant-free composition.

12 Claims, No Drawings

(56) References Cited

U.S. PATENT DOCUMENTS

| | | |
|---|---|---|
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |

(56) References Cited

U.S. PATENT DOCUMENTS

| | | |
|---|---|---|
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo Anna Z. et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |

(56) References Cited

U.S. PATENT DOCUMENTS

| | | |
|---|---|---|
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,741,509 A | 4/1998 | Kushner |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |

(56) References Cited

U.S. PATENT DOCUMENTS

| | | |
|---|---|---|
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |

(56) References Cited

U.S. PATENT DOCUMENTS

| | | |
|---|---|---|
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,859,618 B2 | 10/2014 | Palefsky et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,841,142 B2 | 12/2017 | Nair |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,029,013 B2 | 7/2018 | Tamarkin et al. |
| 10,086,080 B2 | 10/2018 | Tamarkin et al. |
| 10,092,588 B2 | 10/2018 | Tamarkin et al. |
| 10,117,812 B2 | 11/2018 | Tamarkin et al. |
| 10,137,200 B2 | 11/2018 | Tamarkin et al. |
| 10,213,384 B2 | 2/2019 | Tamarkin et al. |
| 10,213,512 B2 | 2/2019 | Tamarkin et al. |
| 10,238,746 B2 | 3/2019 | Tamarkin et al. |
| 10,265,404 B2 | 4/2019 | Tamarkin et al. |
| 10,322,085 B2 | 6/2019 | Tamarkin et al. |
| 10,322,186 B2 | 6/2019 | Tamarkin et al. |
| 10,350,166 B2 | 7/2019 | Tamarkin et al. |
| 10,363,216 B2 | 7/2019 | Tamarkin et al. |
| 10,369,102 B2 | 8/2019 | Tamarkin et al. |
| 10,398,641 B2 | 9/2019 | Tamarkin et al. |
| 10,463,742 B2 | 11/2019 | Tamarkin et al. |
| 10,517,882 B2 | 12/2019 | Tamarkin et al. |
| 10,588,858 B2 | 3/2020 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |

(56) References Cited

U.S. PATENT DOCUMENTS

| | | |
|---|---|---|
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |

(56) References Cited

U.S. PATENT DOCUMENTS

| | | |
|---|---|---|
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0093876 A1 | 4/2012 | Ouster, III |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2018/0000734 A1 | 1/2018 | Tamarkin et al. |
| 2018/0064638 A1 | 3/2018 | Tamarkin et al. |
| 2018/0147218 A1* | 5/2018 | Tamarkin ............... A61K 31/65 |
| 2018/0153804 A1 | 6/2018 | Tamarkin et al. |
| 2018/0193468 A1 | 7/2018 | Tamarkin et al. |
| 2018/0193469 A1 | 7/2018 | Tamarkin et al. |
| 2018/0214558 A1 | 8/2018 | Tamarkin et al. |
| 2018/0235984 A1 | 8/2018 | Eini et al. |
| 2019/0000980 A1 | 1/2019 | Tamarkin et al. |
| 2019/0022000 A1 | 1/2019 | Tamarkin et al. |
| 2019/0022001 A1 | 1/2019 | Tamarkin et al. |
| 2019/0029958 A1 | 1/2019 | Tamarkin et al. |
| 2019/0054106 A1 | 2/2019 | Tamarkin et al. |
| 2019/0076339 A1 | 3/2019 | Tamarkin et al. |
| 2019/0076451 A1 | 3/2019 | Friedman et al. |
| 2019/0091149 A1 | 3/2019 | Tamarkin et al. |
| 2019/0134204 A1 | 5/2019 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |

(56) References Cited

FOREIGN PATENT DOCUMENTS

| | | |
|---|---|---|
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |

(56) References Cited

FOREIGN PATENT DOCUMENTS

| | | |
|---|---|---|
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A2 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |

(56) References Cited

FOREIGN PATENT DOCUMENTS

| WO | WO 2011/039637 A2 | 4/2011 |
|---|---|---|
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2012/100097 A2 | 7/2012 |
| WO | WO 2012/100097 A3 | 7/2012 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |
| WO | WO 2017/089809 A1 | 6/2017 |
| WO | WO 2019/082090 A1 | 5/2019 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.
1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.
242. Allantoin, The Merck Index: An Encyclopedia of Chemicals, Drugs, and Biologicals. 10th edition, Merck & Co., Inc., 1983, p. 39.
Abdullah, G.Z. et al. (Jan. 2013) "Carbopol 934, 940 and Ultrez 10 as viscosity modifiers of palm olein esters based nano-scaled emulsion containing ibuprofen" Pak J Pharm Sci, 26(1):75-83.
Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
Aldara™ (imiquimod) Cream. Highlights of Prescribing Information, Graceway Pharmaceuticals, LLC, Mar. 2007, 29 pages.
Allantoin, Römpp Online, retrieved on Sep. 23, 2015, https://roempp.thieme.de/roempp4.0/do/data/RD-O 1-01552, 5 pages.
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.
Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" Expert Opin Emerging Drugs, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (1983 Feb) "Influence of Water Activity on Growth, Metabolic Activities and Survival of Yeasts and Molds" J Food Prot, 46(2):135-141.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al. "Synthesis of high specific activity [.sup.3 H]-9-cis-retinoic acid and its application for identifying retinoids with unusual binding properties," J. Med. Chem., 1994, 37:408-414.
Brenes, et al., "Stability of Copigmented Anthocyanins and Ascorbic Acid in a Grape Juice Model System", J. Agric Food Chem, 2005, 53(1):49-56 (Abstract Only).
Brisaert, M. et al. (1996) "Investigation on the chemical stability of erythromycin in solutions using an optimization system" Pharm World Sci, 18(5):182-186.
Bronopol, 2-BROMO-2-NURO-1,3-Propanediol, Chemical land, Jul. 17, 2006, retrieved on Jun. 4, 2011, http://chemicalland21.com/specialtychem/perchem/BRONOPOL.html, 4 pages.
Brown et al., "Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.

(56) References Cited

OTHER PUBLICATIONS

Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients. com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only.
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" Dermatol Ther, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.

Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, Report on Carcinogens, Twelfth Edition, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33-1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" J Controlled Rel, 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn'S Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.

(56) References Cited

OTHER PUBLICATIONS

Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).

Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" Pharmaceutical Online [online]. Retrieved from https://www.pharmaceuticalonline.com/doc/pharmaceutical-applications-for-water-activit-..., on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" J Clin Aesthet Dermatol, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
Gelbard et al. "Primary Pediatric Hyperhidrosis: A Review of Current Treatment Options," Pediatric Dermatology, 2008, 25(6):591-598.
Gels, Unc: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" Pharmazie, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%03AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.

(56) References Cited

OTHER PUBLICATIONS

Hallstar® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=I63848,query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/I- ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiencyvirus_hiv_infection/human_immunodeficiency_virus_infection.html?qt=human immunodeficiency virus infection&alt=sh >, 11 pages.
Hwang et al., "Isolation and identification of mosquito repellents in Artemisia vulgaris," J. Chem. Ecol., 1985, 11: 1297-1306.
ICI Americas Inc., "Meaning of HLB Advantages and Limitations" Chapter 1 in the HLB System. A Time-Saving Guide to Emulsifier Selection. Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the pKa of Long-Chain Fatty Acids" J Colloid and Interface Science, 256:201-207.
Karasu et al., "Practice Guideline for the Treatment of Patients with Major Depressive Disorder," Second Edition, Apr. 2000, 78 pages.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" J Drugs Dermatol, 9(8 Suppl):s101-s137.
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6—Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.

(56) References Cited

OTHER PUBLICATIONS

Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of Escherichia coli outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.

Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" Cancer, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb. 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
*Molins PLC v. Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" Polim Med, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," Current Drug Delivery, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "Lamisil®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
Oh et al., "Antimicrobial activity of ethanol, glycerol monolaurate or lactic acid against Listeria moncylogenes,"Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.
OM-Cinnamate, MakingCosmetics.com, retrieved on Sep. 26, 2009, http://www.makingcosmetics.com/sunscreens/OM-Cinnamate-p102.html, 1 page.

(56) References Cited

OTHER PUBLICATIONS

Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.
Palamaras and Kyriakis, "Calcium antagonists in dermatology: a review of the evidence and research-based studies," Derm. Online Journal, 2005, 11(2):8.
Passi et al., "Lipophilic antioxidants in human sebum and aging," Free Radical Research, 2002,36(4):471-477.
Pharmaceutical Benefits Advisory Committee (PBAC) of Australia. PBAC Public Summary Document—Nov. 2014 Meeting (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.
Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.
Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals, Jun. 28, 2013, 1 page.
Promius™ Pharma LLC (2012) Scytera™ (coal tar) Foam, 2%. Product Information Sheet, 1 page.
Prud'Homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and sythetic triphylite," J. Power Sources, 2001, 97-98: 503-507.
Raymond, "Iodine as an Aerial Disinfectant," J. Hygiene, May 1946, 44(5):359-361.
Reaction Rate, Wikipedia, the free encyclopedia, retrieved on Dec. 18, 2011, en.wikipedia.org/wiki/Reaction_rate, 6 pages.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=I# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=I# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=I# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cll-mnOOOI-mnOOOI.htm?q=sucrose%20stearate&t=search&ss=text&p=3# hit.
Rses (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarpotdar, P.P. et al. (Jan. 1986) "Effect of Polyethylene Glycol 400 on the Penetration of Drugs Through Human Cadaver Skin In Vitro" J Pharma Sci, 75(1):26-28.
Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "Malassezia furfur: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," Kirk-Othmer Encyclopedia of Chemical Technology, Jul. 2012, 20 pages.
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.

(56) References Cited

OTHER PUBLICATIONS

Seborrheic Dermatitis, retrieved on Sep. 9, 2010, http://www.cumc.columbia.edu/student/health/pdf/R-S/Seborrhee%20Dermatitis.pdf, 2 pages.
Security Datasheet, Luvitol EHO, Cetearyloctanoat, Nov. 27, 2013, 10 pages.
Sehgal, "Ciclopirox: a new topical pyrodonium antimycotic agent: A double-blind study in superficial dermatomycoses," British Journal of Dermatology, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" J Am Acad Dermatol, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," Langmuir, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT Ltd, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
Solodyn® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).

Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" J Am Oil Chem Soc, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):S475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" Intl J Pharmaceut, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: Formulating Topical Applications—a Practical Guide. Dayan N, Ed., Carol Stream, IL: CT Books, Chapter 9, pp. 233-260.
Tan et al., "Effect of Carbopol and PolyvinYIpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," J. Soc. Cosmet. Chem., Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, filed Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A—B—A) and Brij (A—B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" Invest New Drugs, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3, 4-Didehydroretinoic acid in human keratinocytes are similar and correlate with receptor affinities and transactivation properties," J. Invest. Dermatology, 1994, 102:49-54.

(56) References Cited

OTHER PUBLICATIONS

Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) IN F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E86613576D1, 4 pages.
Trofatter, "Imiqimod in clinical practice", European Journal of Dermatology, Oct./Nov. 1998, 8(7 Supp.):17-19 (Abstract).
Tsai et al.: "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.
Veron et al., "Stability of Minoxidil Topical Formulations", Ciencia Pharmaceutica, 1992, 2(6):411-414 (Abstract).
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Wang and Chen, "Preparation and surface active properties of biodegradable dextrin derivative surfactants," Colloids and Surfaces A: Physicochemical and Engineering Aspects, 2006, 281(1-3):190-193.
Water Jel Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding -rosacea-basics (5 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Weindl et al., "Hyaluronic acid in the treatment and prevention of skin diseases: molecular biological, pharmaceutical and clinical aspects," Skin Pharmacology and Physiology, 2004, 17: 207-213.
Wenninger et al., "International Cosmetic Ingredient Dictionary and Handbook," The Cosmetic, Toiletry, and Fragrance Association, Washington, DC., 1997, vol. 1, 4 pages.
Wermuth, "Similarity in drugs: reflections on analogue design," Drug Discovery Today, Apr. 2006, 11(7/8):348-354.
What Is CP Serum, Skin Biology, retrieved on Dec. 1, 2008, http://web.archive.org/web/20030810230608/http://www.skinbio.com/cpserum.- html, 21 pages.
What Is TSC?, Tuberous Sclerosis Alliance, Jan. 1, 2005, retrieved on Feb. 6, 2014, http://www.tsalliance.org.pages.aspx?content=2, 3 pages.
Williams et al., "Acne vulgaris," Lancet, 2012, 379:361-372.
Williams et al., "Scale up of an olive/water cream containing 40% diethylene glycol monoethyl ether," Dev. Ind. Pharm., 2000, 26(1):71-77.
Williams et al., "Urea analogues in propylene glycol as penetration enhancers in human skin," International Journal of Pharmaceutics, 1989, 36, 43-50.
Wormser et al., "Protective effect of povidone-iodine ointment against skin lesions induced by sulphur and nitrogen mustards and by non-mustard vesicants," Arch. Toxicol., 1997, 71, 165-170.
Wormser, "Early topical treatment with providone-iodine ointment reduces, and sometimes prevents, skin damage following heat stimulus," Letter to the Editor, Burns, 1998, 24:383.
Wrightson, W.R. et al. (1998) "Analysis of minocycline by high-performance liquid chromatography in tissue and serum" J Chromatography B, 706:358-361.
Wu et al., "Interaction of Fatty Acid Monolayers with Cobalt Nanoparticles," Nano Letters, 2004, 4(2): 383-386.
Yamada et al., "Candesartan, an angiotensin II receptor antagonist, suppresses pancreatic inflammation and fibrosis in rats," J. Pharmacol. Exp. Ther., 2003, 307(1):17-23.
Zeichner, J.A. (2010) "Use of Topical Coal Tar Foam for the Treatment of Psoriasis in Difficult-to-treat Areas" J Clin Aesthet Dermatol, 3(9):37-40.
Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).
Declaration Pursuant to 37 C.F.R. §1.132 of Dr. Mohammad Salman, dated Dec. 28, 2015, filed in U.S. Appl. No. 14/074,868.
Declaration Pursuant to 37 C.F.R. §1.132 of Dr. Mohammad Salman, dated May 19, 2016, filed in U.S. Appl. No. 14/074,868.
Declaration Pursuant to 37 C.F.R. §1.132 of Dr. Mohammad Salman, dated Jul. 19, 2016, filed in U.S. Appl. No. 14/074,868.
Hanasono et al., "The Effect of Silicone Gel on Basic Fibroblast Growth Factor Levels in Fibroblast Cell Culture", Arch Facial Plast Surg, vol. 6, pp. 88-23 (2004).
Versagel® M Series, Mineral Oil Moisturizing Gels. Product Bulletin, retrieved from https://archive.org/web/, as archived Oct. 15, 2006, 3 pages.
Allen, The Art, Science, and Technology of Pharmaceutical Compounding, pp. 173-185 (1998).
Allen, The Art, Science, and Technology of Pharmaceutical Compounding, 2nd edition, pp. 250, 251, 263, 267-269, 287, 288, 301-305, tables 16-1 and 16-2 (2002).
Ansel et al., Pharmaceutical Dosage Forms and Drug Delivery Systems, 7th ed., pp. 87-92, 250, 378-380, table 3.3 (1999).

(56) References Cited

OTHER PUBLICATIONS

Attwood et al., Surfactant Systems: Their chemistry, pharmacy and biology, pp. 1-8 (1993).
Bowles et al., "Protection against Minocycline Pigment Formation by Ascorbic Acid (Vitamin C)", Journal of Esthetic Dentistry, vol. 10/No. 4, pp. 182-186 (1998).
Brewer, "Gramicidin", 8 Profiles of Drug Substances, Excipients and Related Methodology, 43 pages (1979).
Calvert, "Foam in Motion", Foams: Physics, Chemistry and Structure, pp. 27-37 (1989).
Donnelly et al., Novel Delivery Systems for Transdermal and Intradermal Drug Delivery, p. 103.
Handbook of Pharmaceutical Excipients 79, 85, 215, 336, 386, 443, 568, 599 (Arthur H. Kibbe ed., 2000).
Healy et al., "Acne vulgaris", Br. Med. J., 308: 831-833, 831 (1994). Johns Hopkins on Acne https://www.hopkinsmedicine.org/health/conditions-and-diseases/acne, 6 pages, 2019.
Kanwar et al., "Treatment of Melasma with Potent Topical Corticosteroids", Dermatology, 188(2):170 (1994). 188(2):170.
Kircik et al., "Formulation and Profile of FMX101 4% Minocycline Topical Foam for the Treatment of Acne Vulgaris," J. Clin. Aesthet. Dermatol., 13(4): 14-21 (2020).
Mah et al., "Irrational Use of Skin-Bleaching Products Can Delay the Diagnosis of Leprosy", International Journal of Leprosy and Other Mycobacterial Diseases, vol. 70, No. 2, pp. 119-121 (2002).
McKetta, Encyclopedia of Chemical Processing and Design: vol. 2—Additives to Alpha, 1st Ed., pp. 214-238 (1977).
The Merck Index: An Encyclopedia of Chemicals, Drugs, and Biologicals 1299-1300, 1638 (13th ed., 2001).
O'Neil, The Merck Index an Encyclopedia of Chemicals, Drugs, and Biologicals, p. 153 (2006).
Olux Prescribing Information (2013).
Pantaris et al., "The lauric (coconut and palmkernal) oils", Vegetable Oils in Food Technology, Chemistry and Technology of Oils and Fats, pp. 157-202 (2002).
Sarkar et al., "A Comparative Study of 20% Azelaic Acid Cream Monotherapy versus a Sequential Therapy in the Treatment of Melasma in Dark-Skinned Patients", Dermatology, 205(3): 249-54 (2002).
Sciarra et al., "Aerosols", Remington: The Science and Practice of Pharmacy, pp. 963-966 (2000).
Tenjarla, "Microemulsions: An Overview and Pharmaceutical Applications", Crit. Rev. Ther. Drug Carrier Sys., 16(5): 461-521 (1999).
Walstra, "Principles of Foam Formation and Stability", Foams: Physics, Chemistry and Structure, pp. 1-15 (1989).

\* cited by examiner

SURFACTANT-FREE, WATER-FREE FORMABLE COMPOSITION AND BREAKABLE FOAMS AND THEIR USES

CROSS REFERENCE TO RELATED APPLICATIONS

This application claims the benefit of priority under 35 U.S.C. § 119(e) to U.S. Provisional Application No. 61/248,144 filed Oct. 2, 2009 and entitled "Surfactant-Free Water-Free Foamable Compositions, Breakable Foams and Their Uses; U.S. Provisional Application No. 61/322,148 filed Apr. 8, 2010 and entitled "Surfactant-Free Water-Free Foamable Compositions, Breakable Foams and Their Uses; U.S. Provisional Application No. 61/349,911 filed May 31, 2010 and entitled "Surfactant-Free Water-Free Foamable Compositions, Breakable Foams and Their Uses; U.S. Provisional Application No. 61/385,385 filed Sep. 22, 2010 and entitled "Surfactant-Free Water-Free Foamable Compositions, Breakable Foams and Gels and Their Uses; U.S. Provisional Application No. 61/331,126 filed May 4, 2010 and entitled "Compositions, Gels and Foams with Rheology Modulators and Uses Thereof; and U.S. Provisional Application No. 61/380,568 filed Sep. 7, 2010 and entitled "Surfactant-Free Water-Free Foamable Compositions and Breakable Foams and Their Uses; all of which are herein incorporated in their entirety by reference.

BACKGROUND

Foam compositions with high amounts of hydrophobic solvents are little known in the art.

Foams and, in particular, oleaginous single-phase foams are complicated systems which do not form under all circumstances. Slight shifts in foam composition, such as by the addition of active ingredients or the removal of any of the essential ingredients, may destabilize the foam.

The prior art teaches oleaginous foam compositions require significant amounts of surface active agents to form and stabilize a foam. These compositions require various standard surfactants, as essential components.

Surfactants are known as essential ingredients in foam compositions because of their amphiphilic properties and because they are considered essential in forming a foam. However, many surfactants are known to be irritating when left on the skin, as they can extract lipids from the skin, thereby damaging skin barrier and exposing the skin to contact with pro-inflammatory factors. (See for example: Effendy, I. and Maibach, H. I. "*Surfactants and Experimental Irritant Contact Dermatitis.*" Contact Dermatol., 33 (1995), 217-225). Many surfactants can also react with unstable active agents and lead to their rapid degradation.

Briefly, the term surfactant has been often loosely used in the art to include substances which do not function effectively as stand alone surfactants to reduce surface tension between two substances or phases. Reduction of surface tension can be significant in foam technology in relation to the ability to create small stable bubbles. In the context herein, the term "standard surfactant" or "customary surfactant" refers to customary non-ionic, anionic, cationic, zwitterionic, amphoteric and amphiphilic surfactants. Many standard surfactants are derivatives of fatty alcohols or fatty acids, such as ethers or esters formed from such fatty alcohols or fatty acids with hydrophilic moieties, such as polyethyleneglycol (PEG). However, a native (non derivatized) fatty alcohol or fatty acid, or wax are not regarded as a standard surfactant.

In the context herein the term "foam adjuvant" includes only fatty alcohols and fatty acids. These are amphiphatic, and essentially hydrophobic with a minor hydrophilic region. For the purposes of forming an emulsion these foam adjuvants, unlike "standard" or "customary surfactants", are not effective as stand-alone surfactants in foamable emulsion compositions, because of their very weak emulsifying capacity on their own. Fatty alcohols and fatty acids have been loosely described as co-surfactants in foamable emulsion compositions, because they assist customary surfactants to boost foam quality, help evolve the foaming properties and because they stabilize the foam in part because of their property as thickeners.

SUMMARY

The present application relates to foamable formulations and foams and their uses comprising hydrophobic solvents. It further relates to hydrophobic solvents with waxes. In particular it relates to waxes that are solid at room temperature. In addition, it relates to formulation with and without an active agent. Surprisingly, the application also relates to foamable formulations and foam without surfactants; and or without surfactants and foam adjuvants; and or without surfactants and polymeric agents; and or without surfactants and foam adjuvants and polymeric agents. In one or more embodiments the hydrophobic solvents are provided as part of a drug carrier. For example certain drugs require hydrophobic solvents in order to solubilize them. In one or more other embodiments, the hydrophobic solvents are provided to facilitate or enhance the transdermal penetration or delivery of a drug. In one or more additional cases, the formulations are provided to have a water barrier effect at a target site, for example where the site of treatment is a damaged skin and the water barrier effect of hydrophobic solvents is desirable. In some embodiments the formulation may have some occlusivity. In some embodiments petrolatum is added to achieve or enhance an occlusive effect. The present application further relates to compositions comprising hydrophobic solvents and their uses.

It is known in the art that foams can easily be formulated based on high amounts of water, in combination with surface active agents, foam adjuvants and polymeric agents. As described in the literature, hydrophobic solvents can have a de-foaming effect which makes the formulation of foams based on hydrophobic solvents-challenging. To overcome this challenge, the prior art requires the use of substantial levels of surfactants that act as efficient foaming agents. The prior art further teaches the incorporation of foam adjuvants, such as fatty alcohols and fatty acids, as foam boosting agents and also the incorporation of polymeric agents (e.g. gelling agents) as foam stabilizers, which can prolong the collapse time of a foam. Waxes may also be introduced into these surfactant based formulations but as will be appreciated, waxes, which are at ambient temperature can easily precipitate. Surface active agents are known to be irritating, especially ionic surface active agents and repeated use can cause dry skin and so it is desirable to reduce their use in pharmaceutical compositions intended to treat skin or mucosa. The technical problems to be overcome in formulating carriers and pharmaceutical compositions with hydrophobic solvent (a) without surfactant; and (b) without surfactant and foam adjuvant; and (c) without polymeric agents and (d) without water are multifold and include finding a suitable substitute for surfactant which provides foam generating properties; finding a suitable replacement that preferably does not need to have a foam adjuvant present with the surfactant (substitute), which if present would inter alia help to boost the foam and as an aid to the surfactant and preferably does not need to have a polymeric agent present with the surfactant (substitute), which if present would inter alia help prolong stability of the foam. It was surprisingly discovered in the present invention, that surface active agents can be advantageously eliminated and replaced by waxes in the context of hydrophobic solvent based-foams. Waxes possess several advantages over other foaming agents such as excellent skin compatibility, almost no chemical reactivity which ensures active ingredients stability and efficient skin occlusion which helps reducing skin water loss and can enhance skin penetration of active agents. Albeit waxes introduce their own additional problems into formulating foamable compositions and foams, including their tendency to solidify and precipitate out from a formulation, and to increase significantly the viscosity of an oleaginous composition, and to block canister valves, against which the formulations need to be designed so that the formulations are not negatively disturbed upon adding an effective amount of propellant and that the formulations are shakable and are homogenous and can readily reform at least upon mild or reasonable shaking prior to use.

In one or more embodiments the drug carrier is formulated for use on sensitive target areas such as sensitive or damages skin areas, wounds, burns, mucosal membranes, body cavities and the eye. In one or more embodiments the composition is intended for use in treatment or prevention of eye infections.

Unexpectedly, it has been discovered that quality oleaginous formulations and foams can be achieved without the presence of significant amounts of standard surfactants. Also surprisingly it has been discovered that quality oleaginous formulations and foams can be achieved without the presence of significant amounts of foam adjuvants (i.e fatty alcohols and fatty acids) known in the art. Further, unexpectedly, it has been discovered that quality oleaginous formulations and foams can be achieved without the presence of significant amounts of standard polymeric agents (e.g. gelling agents). Thus, in one or more embodiments, there is provided a substantially surfactant-free and substantially foam adjuvant-free oleaginous formulation or foam. In one or more preferred embodiments the oleaginous formulations and foams are free of standard surfactants and foam adjuvants. Thus, in one or more embodiments, there is provided a substantially surfactant free and substantially polymeric agent free oleaginous formulation or foam. In one or more preferred embodiments the oleaginous formulations and foams are free of standard surfactants and polymers. Unexpectedly, it has further been discovered that quality oleaginous formulations and foams can be achieved without the presence of significant amounts of standard surfactants, foam adjuvants and polymeric agents known in the art. Thus, in one or more embodiments, there is provided a substantially surfactant free and substantially foam adjuvant free and substantially polymeric agent free oleaginous formulation or foam. In one or more preferred embodiments the oleaginous formulations and foams are free of surface active agents and foam adjuvants and polymeric agents. Moreover, it has been further discovered that these formulations and foams can be achieved over a large range of hydrophobic solvent content. There is thus provided easy to use, stable and non-irritating topical foam formulations, and pharmaceutical compositions thereof, containing a stable or stabilized active pharmaceutical or cosmetic agent having a therapeutic or beneficial effect, intended for treatment of dermal and mucosal tissues free or substantially free of standard surface active agents and foam adjuvants.

In one or more embodiments there is provided a safe and effective foamable carrier composition and foam comprising a hydrophobic solvent, an oleaginous foaming agent comprising a wax and a liquefied or compressed gas propellant. In certain embodiments, the concentration of the propellant is about 1% to about 30% by weight of the total composition. In other certain embodiments, the concentration of the propellant is about 3% to about 25% by weight of the total composition; or about 7% to about 17%; or about 10% to about 14%. In additional embodiments there is provided a safe and effective foamable pharmaceutical or cosmetic composition and foam comprising an effective amount of a pharmaceutical or cosmetic active agent, a hydrophobic solvent, a foaming agent comprising of a wax and a liquefied or compressed gas propellant. The percent by weight is based on weight foamable composition; where the ratio of composition other than propellant to propellant is from about 100:1 to about 100:30; or from about 100:3 to about 100:25; or from about 100:7 to about 100:17; or from about 100:10 to about 100:14 The composition does not contain a surfactant or a foam adjuvant; and the foaming effect is achieved by the addition of the foamer agent, as specified herein. The hydrophobic solvent is present in a substantial amount. In one or more embodiments the hydrophobic solvent is at a concentration between about 40% to about 92% or about 50% to about 90% by weight, or about 40% to about 95% by weight or about 70% to about 90% by weight. In alternative embodiments the formulation is formulated without propellant and delivered as a gel, ointment or rub. The total weight of the foaming agent which is a wax is about 8% to about 50% by weight of a wax. In one or more embodiments the amount of wax is less than 55%; or is less than about 54%; or is less than about 53%; or is less than about 52%; or is less than about 51%; or is less than about 50% by weight; or is less than about 45%; or is less than about 40%; or is less than about 35%; or is less than about 30%; or is less than about 25%; or is less than about 20%; or is less than about 15% by weight. In one or more alternative embodiments the formulation comprises 0% to about 550% wax and about 45% to about 95% hydrophobic solvent. In certain embodiments the wax is about 1% to about 20% and the hydrophobic solvent is about 75% to about 94%. In certain embodiments the wax is about 21% to about 40% and the hydrophobic solvent is about 55% to about 74%. In certain embodiments the wax is about 41% to about 60% and the hydrophobic solvent is about 35% to about 54%. As will be appreciated from the above illustrative examples as the amount of wax is increased the amount of hydrophobic solvent is reduced. Accordingly, differing amounts of wax other than the amounts specified can be contemplated with a parallel increase or decrease in solvent as appropriate. In one or more embodiments their total amount (wax plus solvent) is between about 95% and about 100%. In one or more other embodiments the total amount is between about 92% and about 100%; or between about 90% and about 100%; between about 85% and about 100%; or between about 90% and about 95%; or between about 90% and about 98% or between about 85% and about 95%; or between about 85% and about 98%.

Upon dispensing the foamable carrier composition forms a breakable foam that is stable, yet breaks easily upon application of shear force. In one or more embodiments the composition is used for intradermal delivery of the active agent into the skin with minimal or negligible transdermal delivery. In one or more alternative embodiments a formulation is provided to achieve intra mucosal delivery. In certain embodiments the composition provides for transdermal delivery. In one or more embodiments the composition can be used for prevention of a disease or disorder. The composition or foam is applied to a target surface or area in or on which prevention is sought. In other embodiments the composition or foam is used to treat or ameliorate a disease or disorder. In still further embodiments it may be used to provide a period of remission from the disease or disorder.

According to an embodiment the one or more active agents is selected from the group consisting of adipic acid, an acaricide, an active herbal extract, an age spot and keratose removing agent, an allergen, an alpha hydroxyl acid, an analgesic agent, an androgen, an anesthetic, an anti wrinkle agent, an antiacne agent, an antiaging agent, an antiallergic agent, an antiandrogen agent, an antiapoptotic agent, an antibacterial agent, an antibiotic, an antibiotic agent, an antiburn agent, an anticancer agent, an antidandruff agent, an antidepressant, an antidermatitis agent, an antiedemic anent, an antifungal agent, an antihelminth agent, an antihistamine, an anti-hyperkeratosis agent, an anti-infective agent, an antiinflammatory agent, an antiirritant, an antilipemic agent, an antimicrobial agent, an antimycotic agent, an antioxidant, an antiparasitic agent, an anti-photoaging agent, an anti-photodamaging agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, azelaic acid, benzoyl chloride, benzoyl peroxide, a beta-hydroxy acid, calcitriol, calcium hypochlorite, carbon, a cardiovascular agent, a chemotherapeutic agent, a corticosteroid, a dicarboxylic acid, a dihydrotestosterone inhibitor, a disinfectant, doxycycline, an estrogen, a fungicide, fumaric acid, glycolic acid, a hair growth regulator, a haptene, a herbal extract (comprising an active substance), a hormonal agent, a hormone, a hydroxy acid, an immunogenic substance, an immunomodulator, an immunoregulating agent, an immunostimulant, an immunosuppressant, an immunosuppressive agent, an insect repellent, an insecticide, iron oxide, a keratolytic agent, lactic acid, a lactam, lidocaine, a local anesthetic agent, a lubricating agent, a masking agent, a metal, a metal oxide, minocycline, a mitocide, mometasone fuorate, a neuropeptide, a non-steroidal anti-inflammatory agent, an organo-beryllium compound, an organo-metallic compound, an oxidizing agent, and organo-boron compound, a pediculicide, a peptide, a pesticide, a photodynamic therapy agent, a progesterone, a prostaglandin, a protein, a radical scavenger, a refatting agent, a retinoid, a sedative agent, a scabicide, sebacic acid, a sedative, a sedative agent, a self tanning agent, silicone oxide, silver, a silver compound, a skin protective agent, a skin whitening agent, a steroid, a steroid hormone, a steroidal anti-inflammatory agent, talc, titanium dioxide, a tellurium compound, a testosterone inhibitor, a tetracycline antibiotic, urea, a urea derivative, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D analog, a vitamin D derivative, a vitamin E, a vitamin E derivative, a vitamin F, a vitamin F derivative, a vitamin K, a vitamin K derivative, a wart remover, a wound healing agent, zinc oxide, zirconium oxide. According to a further embodiment the active agent is a tetracycline antibiotic. In certain embodiments the tetracycline is minocycline. In certain embodiments the tetracycline is doxycycline. In certain embodiments the active agent is selected from a group consisting of calcitriol, mometasone fuorate, calcitriol and lidocaine. According to a further embodiment the active agent is chemically stable for at least two months and where the active agent is compatible with the other ingredients. According to a further embodiment the active agent is chemically stable for at least six months; or for at least nine months for at least twelve months; or for at least fifteen months; or for at least eighteen months; or for at least twenty one months; or for at least twenty four months.

As is known to one skilled in the art, in some instances a specific active agent may have more than one activity, function or effect.

In certain embodiments, the inclusion of two or more therapeutic agents in the foamable pharmaceutical composition is desirable.

In one or more embodiments the foamable composition further comprises a fatty alcohol. In one or more embodiments the fatty alcohol is a therapeutically active fatty alcohol. The fatty alcohol can be a straight chain fatty alcohol, a saturated fatty alcohol, an unsaturated fatty alcohol, a hydroxyl substituted fatty alcohol or a branched fatty alcohol.

In an embodiment, the foamable composition further comprises a fatty acid. The fatty acid can be a straight chain fatty acid, a saturated fatty acid, an unsaturated fatty acid, a hydroxyl fatty acid or a branched fatty acid. In an embodiment the fatty acid is a therapeutically active fatty acid.

In an embodiment, the foamable composition comprises a foaming agent which is a wax. The wax can be a liquid wax, a solid wax, an animal wax, a vegetable wax, a mineral wax, a natural wax or a synthetic wax. In an embodiment the wax is selected from a list comprising paraffin wax, beeswax, hydrogenated castor oil or mixtures thereof. In one or more embodiments there is provided a composition comprising a paraffin wax. In one or more embodiments the paraffin wax can have a melting point form about 37° C. In one or more embodiments the paraffin wax comprises of alkane chains of between about $C_{20}H_{42}$ to $C_{40}H_{82}$. In one or more embodiments the alkane chains are substantially straight chain. In some embodiments branched or unsaturated molecules can be present. Branched chains are sometimes referred to as isoparaffins. In one or more embodiments the paraffin wax can be selected from the group consisting of paraffin wax 58-62° C., paraffin wax 51-53° C., and paraffin wax 42-44° C., or mixtures thereof. In one or more other embodiments other melting point ranges can be selected such as 125° F. to 135° F.; 127° F. to 130° F.; 130° F. to 135° F.; 135° F. to 145° F.; 140° F. to 145° F.; 150° F. to 155° F.; 150° F. to 165° F.; 160° F. to 165° F.; or such as 43-46° C.; 46-53° C.; 48-50° C.; 52-54° C.; 53-55° C.; 54-57° C.; 54-58° C.; 58-60° C.; 59-61° C.; 60-62° C.; 62-66° C.; 65-68° C.; or any other similar or relative range(s) or mixtures thereof. In an embodiment the wax is fully refined. In an embodiment it is suitable for cosmetic use. In an embodiment it is suitable for pharmaceutical use. In an embodiment the paraffin wax is soft.

In one or more embodiments the drug carrier is formulated substantially free of short chain alcohols, such as, ethanol, propanol or butanol. In one or more embodiments the drug carrier is formulated essentially free of short chain alcohols. In one or more specific embodiments the drug carrier is formulated essentially free of fatty alcohols and or fatty acids. In one or more other specific embodiments the drug carrier is formulated essentially free of polyols. In one or more other specific embodiments the drug carrier is formulated essentially free of surfactants and or short chain alcohols and or polyols and or fatty acids and or fatty alcohols. In one or more other specific embodiments the drug carrier is formulated substantially free of surfactants and or short chain alcohols and or polyols and or fatty acids and or fatty alcohols.

In one or more embodiments there is provided a composition which is essentially waterless. In one or more embodiments there is provided a composition which is surfactant free. In one or more embodiments there is provided a surfactant free composition that is also foam adjuvant free, and or polymer free. In one or more embodiments there is provided a surfactant free composition that is also free of short chain alcohols and or polyol-free.

In one or more embodiments there is provided a composition comprising a propellant having a vapor pressure between about 10 psi and about 130 psi. In one or more embodiments there is provided a composition comprising a propellant which is hydrocarbon propellant or a hydrofluorocarbon or another environmentally acceptable propellant.

In one or more embodiments there is provided a single phase composition.

In one or more embodiments there is provided a composition comprising a hydrophobic solvent which is a liquid oil, selected from the group consisting of hydrocarbon oils, mineral oil, liquid paraffin, isoparaffin, polyalphaolefin, polyolefin, polyisobutylene, synthetic isoalkane, isohexadecane isododecane, ester oils, alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumarate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystarate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isosteary citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isosteary salicylate, isosteary tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate and triisocetyl citrate, liquid triglycerides, oils of plant origin, alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil, an essential oil, PPG alkyl ethers, PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether and PPG-11 stearyl ether. Preferred PPG alky ethers according to the present invention include PPG-15 stearyl ether, PPG-2 butyl ether and PPG-9-13 butyl ether, oils from animal origin, herring oil, cod-liver oil and salmon oil, therapeutic oil, manuka oil, rosehip oil, tea tree oil, basil oil, camphor oil, cardamom oil, carrot oil, citronella oil, clary sage oil, clove oil, cypress oil, frankincense oil, ginger oil, grapefruit oil, hyssop oil, jasmine oil, lavender oil, lemon oil, mandarin oil, marjoram oil, myrrh oil, neroli oil, nutmeg oil, petitgrain oil, sage oil, tangerine oil, vanilla oil verbena oil, silicone oils, cyclomethicone, dimethicone, polyalkyl siloxane, polyaryl siloxane, polyalkylaryl siloxane, polyether siloxane copolymer, poly(dimethylsiloxane)-(diphenyl-siloxane) copolymer, dimethyl polysiloxane, epoxy-modified silicone oil, fatty acid-modified silicone oil, fluoro group-modified silicone oil, methylphenylpolysiloxane, phenyl trimethicone, polyether group-modified silicone oil cyclomethicone, cyclotetrasiloxane, cyclohexasiloxane, phyenyltrimethicone, Dow corning 246 Fluid (d6+d5) (cyclohexasiloxane & cyclopentasiloxane), Dow Corning 244 Fluid (cyclotetrasiloxane), Cyclomethicone 5-NF (cyclopentasiloxane), stearyl dimethicone, phenyltrimethicone, cetyl dimethicone, caprylyl methicone, PEG/PPG 18/18 dimethicone, or dimethiconol, capric/caprylic triglycerides, cyclomethicone; isopropyl myristate, isopropyl palmitate, PPG-15 stearyl ether; octyldodecanol; isohexadecanol, diisopropyl adipate; cetearyl octanoate; MCT oil; heavy mineral oil; light mineral oil; coconut oil and soybean oil, an unsaturated or polyunsaturated oil, a diglyceride, a PPG alkyl ether or mixtures thereof.

According to additional embodiments there is provided a method of producing a foamable composition, including:
1. providing a foamable therapeutic composition including a therapeutic agent at a therapeutically effective concentration, a hydrophobic solvent, for example, at a concentration of about 50% to about 90% by weight and a foaming agent including a wax;
2. introducing the foamable composition in an aerosol packaging assembly, comprising of a container, suitable for containing a pressurized product and a valve, capable of extruding a foam; and
3. introducing to the aerosol packaging assembly a liquefied or compressed gas propellant at a concentration.

According to additional embodiments the formulation comprises about 1% to about 18% wax and about 80% to about 94% hydrophobic solvent. In further embodiments wax may be in excess of 18%.

In one or more embodiments there is provided a method of preventing or treating or alleviating a dermatological or mucosal disorder, comprising: applying a substantially surfactant free foamable composition to a surface having or anticipated to have a dermatological or mucosal disorder or disease in need of treatment. In one or more embodiments the active agent is a placebo.

In one or more embodiments there is provided use of a substantially surfactant free foamable composition for preventing or treating or alleviating a dermatological or mucosal disorder.

In one or more embodiments the disorder is selected form the group consisting of abscess, acne, acne conglobata, acne fulminans, acne vulgaris, acne scars, acute febrile neutrophilic dermatosis, acute lymphangitis, allergic contact dermatitis, alopecia, athlete's foot, atopic dermatitis, bacterial skin infections, baldness, basal cell carcinoma, blisters, bromhidrosis, bullous pemphigoid, burn, calluses candidiasis, carbuncles, cellulitis, chemical burns, chicken pox, cholesteatoma, cholinergic urticaria, chronic effects of sunlight, cold sores, cold urticaria, comedones, corns, creeping eruption, cutaneous abscess, cutaneous larva migrans, cutaneous myiasis, dark spots, delusional parasitosis, Dercum disease, dermatitis, dermatitis herpetiformis, dermatological pain, dermatological inflammation, dermographism, dermatophytoses, drug eruptions and reactions, dyshidrotic eczema, ectodermal dysplasia, eczema, ecthyma, epidermoid cyst, epidermal necrolysis, erysipelas, erysipelas, erythrasma, exfoliative dermatitis, erythema multiforme, erythema nodosum, folliculitis, fungal nail infections, fungal skin infections, furuncles, gangrene, genital herpes, granuloma annulare, head lice, hidradenitis suppurativa, hives, folliculitis, hirsutism, hyperhidrosis, hypohidrosis, ichthyosis, impetigo, inflammatory acne, ingrown nails, intertrigo, irritant contact dermatitis, ischemic necrosis, itching, jock itch, Kaposi's sarcoma, keratosis pilaris, lichen simplex chronicus, lichen planus, lichen sclerosus, lymphadenitis, lymphadenitis, lymphangitis, malignant melanoma, mastocytosis, measles, melanoma, melanoma, miliaria, moles, molluscum contagiosum, MRSA, necrotizing subcutaneous infection, necrotizing fasciitis, necrotizing myositis, nodular papulopustular acne, non-inflammatory acne, nummular dermatitis, oral herpes, panniculitis, parapsoriasis paronychia, parasitic skin infections, pemphigus, photoallergy, photo-damage, photo-irritation, photosensitivity, papules, pediculosis, perioral dermatitis, pimples, pityriasis rosea, pityriasis Lichenoides, pityriasis rosea, pityriasis rubra pilaris, poison ivy, poison oak post-operative or post-surgical skin conditions, pressure ulcers, pressure urticaria, pruritis, pseudofolliculitis barbae, psoriasis, PUPPP, purpura, pustules, pyogenic granuloma, rash, ringworm, rosacea, roseola, rubella, scabies, scalded skin syndrome, scarring, scleroderma, sebaceous cyst, seborrheic dermatitis, seborrheic keratosis, shingles, skin aging, skin cancer, skin neoplasia, skin neoplasms, skin rash, skin ulcers, squamous cell carcinoma, staphylococcal scalded skin syndrome, stasis dermatitis, Stevens-Johnson syndrome, sunburn, sun spots, thermal burns, tinea corporis, tinea cruris, tinea pedis, tinea versicolor, toxic epidermal necrolysis, trauma or injury to the skin, varicella zoster virus, vitamin D deficiency, viral skin infections, vitiligo, warts, water hives, wrinkles, xerosis, yeast skin infections and zoster.

According to further embodiments there is provided a method of preventing, treating ameliorating or eliminating a disorder by selecting and releasing on to a convenient surface a safe and effective pharmaceutical or cosmetic foamable composition comprising an effective amount of a pharmaceutical or cosmetic agent, a hydrophobic solvent, a foaming agent comprising a wax and a liquefied or compressed gas propellant at a concentration of about 1% to about 30% by weight of the total composition; directing the released foam on to a target on a patient in need or anticipated need; applying a shear force to and spreading the foam over the target surface such that after a simple rub the foam is no longer visible to the naked eye as it is absorbed rapidly on to the target surface.

According to one of more further embodiments the disorder treated by the foamable composition is selected from the group consisting of a dermatose, a dermatitis, a vaginal disorder, a vulvar disorder, an anal disorder, a disorder of a body cavity, an ear disorder, a disorder of the nose, a disorder of the respiratory system, a bacterial infection, a fungal infection, a viral infection, dermatosis, dermatitis, parasitic infections, disorders of hair follicles and sebaceous glands, scaling papular diseases, benign tumors, malignant tumors, reactions to sunlight, bullous diseases, pigmentation disorders, disorders of cornification, pressure sores, disorders of sweating, inflammatory reactions, xerosis, ichthyosis, an allergy, a burn, a wound, a cut, a chlamydia infection, a gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, a yeast infection, vulvar dystrophy, vulvar intraepithelial neoplasia (VIN), contact dermatitis, osteoarthritis, joint pain, an hormonal disorder, a pelvic inflammation, endometritis, salpingitis, oophoritis, genital cancer, cancer of the cervix, cancer of the vulva, cancer of the vagina, vaginal dryness, dyspareunia, an anal and rectal disease, an anal abscess/fistula, anal cancer, an anal fissure, an anal wart, Crohn's disease, hemorrhoids, anal itch, pruritus ani, fecal incontinence, constipation, polyps of the colon and rectum.

DETAILED DESCRIPTION

Foamable Composition and Foam Properties

The ability to achieve quality foam with a substantial concentration of hydrophobic solvent without a surfactant and without a foam adjuvant and without a polymer is surprising, because usually, such solvents are not prone to creating a foam. The challenge is not just to achieve a quality foam but also to attain a formulation that will satisfy a plurality of two, three, four, five, six or more of the following property specifications simultaneously.

Notably, the pressurized composition is flowable and releases a foam freely, even though it might be expected that such concentrations of wax would make the hydrophobic solvent very viscous or 'semi-solid'.
1. Uniformity: The composition should be formulated so that it is and can remain uniform upon shaking and that it can reconstitute upon shaking without phase separation or precipitation over a reasonable time. This property is of importance when the product is intended to be a pharmaceutical product.
2. Flowability: The composition, when placed in an aerosol container and pressurized with a propellant should be flowable such that it can be expelled through the canister valve. It should preferably also be shakable inside the container. These requirements create a formulation challenge, because non-viscous flowable and shakable compositions are prone to undergo phase separation or precipitation.
3. Quality: Upon release from the can, the composition should generate a foam of good or excellent quality having low density and small bubble size.
4. Stability/Breakability: The fine balance between stability and breakability of the foam coming out of the container is very delicate: on one hand the foam should preferable not be "quick breaking", i.e., it should be at least short term stable upon release from the pressurized container and not break as a result of exposure to skin temperature; and on the other hand, it should be "breakable", i.e., it should spread easily, break down and absorb into the skin or membrane upon application of mild shear force.
5. Skin Feeling: To ensure patient compliance the skin feeling after application should be pleasant, and greasy or waxy residues should be minimal.
6. Non-irritating: The above requirements should be achieved with the awareness that formulation excipients, especially surfactants, can be irritating, and should preferably be eliminated from the composition or reduced as much as possible.
7. Delivery: Finally, the composition should also be designed to ensure efficient delivery of a therapeutic agent into the target site of treatment.
8. Compatibility: The components of the composition should be compatible and not react with an active agent.

Based on extensive investigations and trial and error experiments, it has been found that such properties can be achieved for formulations as described below and which are further advantageous because of the ability of hydrophobic solvents to dissolve or suspend certain active agents while providing an environment for the active agent which assists in preventing their degradation.

Compositions

All % values are provided on a weight (w/w) basis.

In one or more embodiments there is provided a foamable carrier composition including:
1. a hydrophobic solvent
2. a foaming agent comprising a wax;
3. a liquefied or compressed gas propellant.

Waxes

In one or more embodiments the wax includes a paraffin wax. In one or more embodiments the paraffin wax includes a paraffin wax having a melting point or melting point range somewhere in between about 47° C. to about 64° C. In one or more embodiments the paraffin wax includes a paraffin wax having a melting point of about 58° C. to 62° C. In one or more embodiments the paraffin wax includes a paraffin wax having a melting point of about 51° C. to 53° C. In one or more embodiments the paraffin wax includes a paraffin wax having a melting point of about 42° C. to 44° C. In one or more embodiments the wax includes a beeswax. In one or more embodiments the wax includes a hydrogenated caster oil, which is a wax.

Paraffin waxes are primarily mixtures of solid saturated hydrocarbons having the general formula $CnH(2n+2)$.

Unexpectedly it was found that paraffin waxes could form quality foam with oils without the assistance of surfactants, and/or foam adjuvants and/or polymers. Without being bound to a specific theory, the ability of paraffin wax to facilitate the formation of quality stable breakable foam with oils appears to relate to its unique molecular structure and size and resultant Van der Waals forces. Paraffin waxes are comprised primarily of long straight chain molecules having chains consisting of between about 20 to about 40 carbons. Higher melting point paraffin waxes will be expected to have a higher proportion of longer chains than lower melting waxes. Introduction of branched chains may result in a reduction of melting point. Without being bound to a specific theory, such long hydrocarbon chains exhibit momentary asymmetry in the electron distribution resulting in temporary dipoles that induce similar dipoles in nearby molecules (Van der Waals forces). This phenomenon is especially prevalent in long molecules like paraffin wax, and less so in the shorter (but otherwise similar) mineral oil.

Apparently, the temporary dipole (+) - - - (−) in one molecule induces a dipole in the opposite direction (−) - - - (+) in another molecule. This interaction occurs between the paraffin wax and other compounds within the composition. Thus, it may be concluded that molecular ranges within about C20-C40 have preferred capabilities in terms of stable breakable foam formation.

There seems to be another coinciding property of paraffin wax that may be involved with foam stability, which is its critical surface tension ("CST"). Hydrophobic behavior of surfaces is generally considered to occur when CST is less than 35 mN/m. At first, the decrease in critical surface tension is associated with oleophilic behavior, i.e. the wetting of the surfaces by hydrocarbon oils.

Paraffin wax is unique among other hydrocarbon chains by having a CST of about 25 (e.g., 25.5), which is about in the middle of the hydrophobic range. Thus, paraffin waxes are somewhat amphipatic which may also contribute to foam stability. Notably, in comparison to longer hydrocarbons, such as polyethylene and polypropylene, paraffin wax is much more hydrophobic, thereby decreasing the surface tension of the hydrophobic solvents in the composition and facilitating foam formation and stabilization (the CST of polypropylene 31.0 and polyethylene 33.0).

The chain length amongst other things is responsible for the different melting points of the paraffin waxes. It was found that higher melting point paraffin waxes could form quality foams with less material than lower melting point fractions. Without being bound by any theory, it may be postulated that since high melting point fractions have longer chains, the Van der Vaals forces are greater so lower amounts can facilitate the formation of quality short term thermally stable foams. Thus, in an embodiment of the present invention, there is provided a paraffin wax, having CST of about 25; or between about 20 to about 30; or about 22 to about 28; about 23 to about 27; about 20 to about 30. In an embodiment selecting the CST of a wax is a means of providing a foamable formulation with a hydrophobic solvent that will generate a foam of quality that is at least short term stable.

Hydrogenated castor oil consists mainly of triglycerides of hydroxystearic acid and is a solid wax.

Beeswax contains, for example, a high proportion of wax esters (about 35 to 80%), which are linear monoesters of straight-chain fatty alcohols with even-numbered carbon chains from C24 to C36 esterified with straight-chain fatty acids such as 16:0 and 18:0 fatty acids some with hydroxyl groups in the ω-2 and ω-3 positions. The wax esters can consist of C40 to C46 molecular species, Also present are free acids (about 14%) and carbohydrates (about 12%) as well as approximately 1% free wax alcohols and stearic esters of fatty acids.

In one or more embodiments, the wax is a polyolefin such as polyethylene, polypropylene, polymethylpentene, polybutene, a polyolefin elastomer, polyisobutylene, ethylene propylene rubber, ethylene propylene diene Monomer (M-class) rubber, polyethylene terephthalate, polydicyclopentadiene, linear polyolefins, branched polyolefins, cyclic polyolefins, low density polyolefins, high density polyolefins, polyolefins with a low molecular weight, polyolefins with a high molecular weight, halogenated polyolefins and the like and mixture thereof.

In one or more embodiments, the wax is polyvinyl chloride, polyvinylidene chloride, polyvinylidene fluoride, polyvinyl fluoride, polytetrafluoro ethylene, polychlorotrifluoro ethylene, polystyrene, polybutadiene, polyisoprene, polychloroprene, polymethylpentene and the like and mixture thereof.

In one or more certain embodiments a fatty alcohol and or a fatty acid may be added to the wax.

In one or more embodiments oily emollients are added to provide or improve a pleasant skin feeling, and or lubricating effect with reduced friction. In one or more embodiments volatile silicones are added to reduce greasy feeling. In one or more embodiments various waxes are added to improve rheology or stabilize foam structure.

Surfactants play a role in foam formation and induce foam stability. In one or more embodiments the formulation is substantially or essentially free of surfactants. In one or more embodiments a small amount of surfactant may be added, preferably less than 1%. Scientific literature is not always accurate and may loosely or even inaccurately describe a substance as a surfactant. For example, fatty alcohols or fatty acids (in the absence of a base) when used in combination with classic surfactants have sometimes been referred to as surfactants, whereas at best they merely function as an aid to classic surfactant and may loosely be termed as a co-surfactant but they are not able to stabilize an emulsion and achieve a stable foam emulsion on their own without the presence of a true surfactant. (For more detail see "co-surfactant" below.) In the context of the present application such fatty acids and fatty alcohols are not surface active agents but are foam adjuvants. Similarly propoxylated lanolin oil derivatives have been loosely referred to as surfactants. In the context herein they are emollients (not surfactants). In one or more embodiments the composition is substantially free of foam adjuvants and comprises less than about 5% final concentration of foam adjuvants, preferably less than 2%, more preferably less than 1%. Where a formulation includes insignificant amounts of foam adjuvants it is considered to be essentially free of them. In one or more embodiments the composition is essentially free of foam adjuvants such as fatty alcohols and or fatty acids. In one or more embodiments a small amount of foam adjuvant may be added, preferably less than 1%. In one or more embodiments the composition is essentially free of propoxylated lanolin oil derivatives. In one or more embodiments the composition is essentially free of ethoxylated lanolin oil derivatives. In further embodiments the compositions are free of such derivatives. In one or more certain embodiments the composition is free of PPG, lanolin oils, such as PPG 40 PEG 60 lanolin oil. In one or more embodiments foam adjuvants (i.e. fatty alcohols and fatty acids) and additives (such as SiO2 which acts as a thickener and can provide thixotropy) can be added to improve rheology or stabilize foam structure or as a protective agent. In one or more embodiments antioxidants can be used to prevent degradation/oxidation, for example, butylated hydroxytoluene, which is a fat soluble antioxidant.

In one or more embodiments the foamable composition is substantially surfactant and foam adjuvant free. In one or more other embodiments it is essentially free of any surfactants and foam adjuvants.

Upon release from an aerosol container, the foamable composition forms an expanded breakable foam suitable for topical administration.

The foamable composition is suitable for administration to various body areas, including, but not limited to the skin, a body surface, a body cavity, a mucosal surface, e.g., the mucosa of the nose, mouth and eye, the ear, the respiratory system, the vagina or the rectum (severally and interchangeably termed herein "target site").

In one or more embodiments, the composition is waterless. By waterless is meant that the composition contains no or substantially no, free or unassociated or absorbed water. It will be understood by a person of the art that to the extent the waterless solvents and substances miscible within them of the present disclosure are hydrophilic, they can contain water in an associated or unfree or absorbed form and may absorb water from the atmosphere.

According to one or more embodiments, the foamable composition further comprises one or more cosmetic active agents or a pharmaceutical active agents (severally and interchangeably termed herein "active agent").

In one or more embodiments the carrier comprises an active agent which degrades in the presence of water, and in such cases the presence of water in the composition is clearly not desirable. Thus, in certain preferred embodiments, the composition is waterless. In other embodiments the active agent may tolerate the presence of a small amount of water and the waterless composition is substantially non-aqueous. The term "substantially non-aqueous" is intended to indicate that the waterless composition has water content preferably below about 2%, such as, below about 1.5%, below about 1%; or below about 0.5%. In certain embodiments the amount of water is about or less than about 5%. Where water is present the formulation may be an emulsion or may form micelles or a colloid.

In one or more embodiments there is provided a foamable therapeutic composition including:
1. an active agent;
2. a hydrophobic solvent between about 40% to about 92% by weight;
3. a foaming agent comprising between about 8% to about 50% by weight of wax;
4. a liquefied or compressed gas propellant wherein the percent by weight is based on weight foamable composition; wherein the ratio of composition other than propellant to propellant is from about 100:3 to about 100:30; and wherein upon dispensing the foamable carrier composition forms a breakable foam that is stable, yet breaks easily upon application of shear force.

In one or more embodiments the hydrophobic solvent range is between about 35% to about 95%; about 40% to about 95%; about 40% to about 92%; about 45% to about 92%; about 50% to about 92%; about 55% to about 92%; about 60% to about 92%; about 40% to about 90%; about 45% to about 90%; about 50% to about 90%; about 55% to about 90%; about 60% to about 90%; about 40% to about 85%; about 45% to about 85%; about 50% to about 85%; about 55% to about 85%; about 60% to about 85% about 40% to about 80%; about 45% to about 80%; about 50% to about 80%; about 55% to about 80%; about 60% to about 80%; about 40% to about 70%; about 45% to about 70%; about 50% to about 70%; about 55% to about 70%; or about 60% to about 70%

In one or more embodiments the wax range is between about 5% to about 52%; about 8% to about 52%; about 10% to about 52%; about 15% to about 52%; about 20% to about 52%; about 25% to about 52%; about 30% to about 52%; 5% to about 50%; about 8% to about 50%; about 10% to about 50%; about 15% to about 50%; about 20% to about 50%; about 25% to about 50%; about 30% to about 50%; 5% to about 45%; about 8% to about 45%; about 10% to about 45%; about 15% to about 45%; about 20% to about 45%; about 25% to about 45%; or about 30% to about 45%; 5% to about 40%; about 8% to about 40%; about 10% to about 40%; about 15% to about 40%; about 20% to about 40%; about 25% to about 40%; or about 30% to about 40%;

In one or more embodiments, at least a portion of the therapeutic agent is suspended. In one or more embodiments the therapeutic agent is dissolved. In one or more embodiments it is partly suspended and partly dissolved. In one or more embodiments the suspended agent is evenly or homogenously distributed throughout the composition. In one or more embodiments homogeneity is achieved after shaking shortly before intended use.

Formulations containing high amounts of hydrophobic solvents (such as mineral oil) are not prone to foaming. For example, it has been found that a formulation containing only mineral oil and propellants did not produce foam. Similarly, formulations containing paraffin wax and propellant only did not produce foam. It has also been found that when a propellant is added to combinations of one or more different oils with relatively low levels of one or more different waxes in the absence of foam stabilizers such as surfactants or foam adjuvants, foams were mostly not produced at all or were not of quality and collapsed rapidly. In other words they were not short term stable and breakable quality foams.

Suprisingly, when propellant was added to formulations containing a combination of certain hydrophobic solvents and waxes, preferably paraffin wax, together having a total weight of about 100% or about 95%, short term stable yet breakable quality foams were successfully produced in the absence of customary surfactants and in the absence of customary foam adjuvants. Thus, unexpectedly it was discovered that wax has foaming or foam boosting properties of its own when formulated with hydrophobic solvents, such as mineral oil, and provides breakable short stable foams of good quality. The amount of wax required depends on the type of wax selected. In general, the amounts of paraffin waxes having a higher melting point range needed to achieve a good quality foam can be less than the amounts of paraffin waxes having a lower melting point range. Moreover, in general, higher amounts of hydrogenated caster oil wax or beeswax are needed to achieve a foam compared to paraffin wax. Similarly, higher amounts of beeswax are needed to achieve a foam compared to hydrogenated caster oil wax For example, formulations containing between about 50% and about 90% heavy mineral oil and from about 10% to about 50% paraffin wax (having a melting point of about 51-53° C.) produced good to excellent quality foams that had a collapse time of about more than 2 minutes or about more than 3 minutes at 36° C. Excellent foams that were stable for more than 3 minutes were obtained in formulations having from about 15% to about 50% paraffin wax 51-53° C. On the other hand formulations with paraffin wax 51-53° C., 5% produced poor foam whilst 7.5% generated only fairly good foam.

Also formulations containing about 60% heavy or light mineral oil and about 40% paraffin wax (having a melting point of about 42-44° C.) produced excellent quality foams that displayed a collapse time of about or more than 1 minute or more than 2 minutes at 36° C. depending on the propellant. On the other hand formulations with 20% of 42-44 resulted in a poor quality.

In an embodiment foam quality may be improved by increasing the propellant, by say aliqots of 2% or 4%, for example, from 8% to about 12%. The actual amount of propellant increase that is suitable should be titrated from formulation to formulation.

Furthermore, formulations containing between about 80% and about 90% heavy mineral oil and between about 10% and about 20% paraffin wax (having a melting point of about 58-62° C.) produced excellent quality foams, having low density (between 0.1 and 0.2 g/mL) that exhibited a collapse time of about or more than 3 minutes at 36° C.

Furthermore, different oleaginous foam formulation consisting of 80% of various oils and 20% paraffin wax (51-53° C.), or consisting of 80% heavy mineral oil and 20% paraffin wax (51-53° C.) and various propellants or consisting of heavy mineral oil between about 60%-80% and various waxes between about 20%-40% produced quality foams that showed a collapse time of about or more than 2 minutes or more than 3 minutes at 36° C.

Furthermore, oleaginous foam formulation consisting of 80% heavy mineral oil and 20% paraffin wax (51-53° C.) showed physical stability in accelerated stability tests. There was hardly any change in foam quality, density or collapse time after 2 months of storage at 40° C. A decrease in formulation shakability was detected which may be explained by a partial solidification of the wax content with time. It may be overcome inter alia by increasing the propellant concentration of the formulation to about 12%, or by using a propellant having a higher vapor pressure such as propellant comprising propane.

These results were surprising as no known foam stabilizing agent such as surfactants was present. Moreover, no fatty alcohol or fatty acid was needed, and formulations containing only hydorphobic solvents and waxes generated thermally stable quality foams.

It has further been found that for high concentrations of wax, the inclusion of higher amounts of propellant was found useful in order to improve the flowability of the formulation within the canister, as indicated by the shakability results.

In one or more embodiments there is provided a foamable carrier composition comprising a solvent, a wax and a liquefied or compressed gas propellant wherein the formulation provides upon dispensing a breakable foam of quality which has a collapse time at 36° C. of about or more than 1 minute. In one or more embodiments, the solvent is a hydrophobic solvent. In one or more embodiments, the hydrophobic solvent is mineral oil. In one or more embodiments, the wax is a paraffin wax. In one or more embodiments, the wax is a hydrogenated caster oil. In one or more embodiments, the wax is a beeswax.

In one or more embodiments there is provided a foamable carrier composition comprising a hydrophobic solvent between about 50% to about 90% by weight of formulation, a wax between about 10% to about 50% by weight of formulation and a liquefied or compressed gas propellant wherein the formulation provides upon dispensing a breakable foam of quality which has a collapse time at 36° C. of about or more than 1 minute. In one or more embodiments the composition further comprises one or more active agents.

In one or more embodiments there is provided a foamable carrier composition comprising a solvent selected from a list consisting of a capric/caprylic triglycerides, PPG-15 stearyl ether, isopropyl palmitate, isopropyl myristate, octyldodecanol, between about 50% to about 90% by weight of formulation, wax between about 10% to about 50% by weight of formulation and a liquefied or compressed gas propellant wherein the formulation provides upon dispensing a breakable foam of quality which has a collapse time at 36° C. of about or more than 1 minute. In one or more embodiments the composition further comprises one or more active agents.

In one or more embodiments there is provided a foamable carrier composition comprising a hydrophobic solvent between about 50% to about 90% by weight of formulation, wax between about 10% to about 50% by weight of formulation and a liquefied or compressed gas propellant where the propellant is hydrocarbon or hydrofluorocarbon propellant which may selected from a the group consisting of propane, butane, isobutene or mixtures of two or three thereof, AP-70, A-46, Dymel 134a or mixtures of two or more thereof, wherein the formulation provides upon dispensing a breakable foam of quality with a collapse time at 36° C. of about or more than 1 minute. In one or more embodiments the composition further comprises one or more active agents.

In one or more embodiments inclusion of higher amounts of propellant improves the flowability of the formulation. In one or more embodiments the improvement is more pronounced where there are high amounts of waxes within the canister.

Furthermore, the formulations of the present invention comprising a hydrophobic solvent, for example, mineral oil, and a wax, for example, a paraffin wax 51-53° C., and a propellant in an effective amount can provide foams of good quality in the presence of various active ingredients. In the context herein active pharmaceutical ingredients and active cosmetic ingredients are collectively termed "active agent" or "active agents". Formulations, for example, comprising minocycline HCl, mometasone fuorate, calcitriol and lidocaine produced breakable foams of quality which are stable and have a collapse time at 36° C. of about or more than 1 minute.

In one or more embodiments there is provided a foamable carrier composition comprising a solvent, a wax and a liquefied or compressed gas propellant and one or more active ingredients wherein the formulation provides upon dispensing a breakable foam of quality which has a collapse time at 36° C. of about more than 1 minute. In one or more embodiments, the solvent is a hydrophobic solvent. In one or more embodiments, the hydrophobic solvent is mineral oil. In one or more embodiments, the wax is a paraffin wax. In one or more embodiments, the wax is a hydrogenated caster oil. In one or more embodiments, the wax is a beeswax.

In one or more embodiments, the active agent is a tetracycline. In one or more embodiments, the tetracycline active agent is a minocycline HCl. In one or more embodiments, the active agent is a benzoyl peroxide. In one or more embodiments, the active agent is mometasone fuorate. In one or more embodiments, the active agent is calcitriol or another vitamin D derivative. In one or more embodiments, the active agent is lidocaine.

In one or more embodiments, the composition is essentially free of polyols.

In one or more embodiments, composition is capable of providing intradermal delivery of the active agent into the skin with minimal or negligible transdermal delivery.

In one or more embodiments, the composition is for use in eye infections.

In one or more embodiments, the composition is physically stable for at least two months.

In one or more embodiments, there is provided a substantially surfactant and foam adjuvant free composition comprising:
  a) about 50% to about 90% by weight of a hydrophobic solvent;
  b) an oleaginous foaming agent comprising
    i) about 10% to about 50% by weight of paraffin wax;
  c) an active agent,
  d) a liquefied or compressed gas propellant
    wherein the percent by weight is based on weight of foamable composition; wherein the ratio of composition other than propellant to propellant is from about 100:3 to about 100:30;
    wherein upon dispensing the foamable carrier composition forms a breakable foam that is stable, yet breaks easily upon application of shear force, and
    wherein the active agent is compatible with in the formulation; wherein the formulation provides upon dispensing a breakable foam of quality which has a collapse time at 36° C. of about more than 1 minute.

It was observed that when a more solid paraffin wax was used the stability of the formulation was improved yet shakability decreased (compare samples 023, 024 to samples 031, 032 respectively and also compare samples 035 to sample 013 respectively). It was also observed that the when light mineral oil was used as opposed to heavy mineral oil the shakability was improved (compare samples 029, 030 to samples 023, 024 respectively). It may be, without being bound by any theory, that apart from any other chemical differences between the different waxes, the observations may be accounted for in part or entirety by the longer wax chain lengths in the higher melting point paraffin waxes.

Hydrophobic Solvent

In an embodiment, the composition of the present invention comprises at least one hydrophobic organic solvent. A "hydrophobic organic solvent" (also termed "hydrophobic solvent") as used herein refers to a material having solubility in distilled water at ambient temperature of less than about 1 gm per 100 mL, more preferably less than about 0.5 gm per 100 mL, and most preferably less than about 0.1 gm per 100 mL. It is liquid at ambient temperature. The identification of a "hydrophobic solvent", as used herein, is not intended to characterize the solubilization capabilities of the solvent for any specific active agent or any other component of the foamable composition. Rather, such term is provided to aid in the identification of materials suitable for use as a hydrophobic solvent in the foamable compositions described herein.

In one or more embodiments the hydrophobic solvent is present at a concentration of about 40% to about 90%; or about 50% to about 95%; or about 60% to about 95% or about 65% to about 90%; or about 70% to about 90% or about 75% to about 85%.

In one or more embodiments, the composition of the present invention comprises at least one hydrophobic solvent, selected from the group consisting of a mineral oil, a hydrocarbon oil, an ester oil, a liquid triglyceride oil, an oil of plant origin, an oil from animal origin, an unsaturated or polyunsaturated oil, a diglyceride, a PPG alkyl ether and a silicone oil.

As exemplified herein, members of each of the above listed groups of hydrophobic solvents have been found to be compatible with hydrophobic tetracyclines, such as minocycline and doxycycline.

Non-limiting examples of hydrocarbon oils include mineral oil, liquid paraffin, an isoparaffin, a polyalphaolefin, a polyolefin, polyisobutylene, a synthetic isoalkane, isohexadecane and isododecane.

Non-limiting examples of ester oils include alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, his (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystarate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isosteary citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isosteary salicylate, isosteary tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate and triisocetyl citrate.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Non-limiting examples of PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether and PPG-11 stearyl ether. Preferred PPG alky ethers according to the present invention include PPG-15 stearyl ether, PPG-2 butyl ether and PPG-9-13 butyl ether.

Non-limiting examples of oils from animal origin include herring oil, cod-liver oil and salmon oil.

The hydrophobic solvent may be an emollient, i.e., a hydrophobic liquid having a softening or soothing effect especially to the skin. In some embodiments the liquid oil may contain a solid or semi solid hydrophobic matter at room temperature.

Essential oil, which is usually a concentrated, hydrophobic liquid containing volatile aroma compounds from plants usually conveying characteristic fragrances. Non limiting examples include lavender, peppermint, and eucalyptus. A therapeutic oil is a hydrophobic liquid which is said to have a therapeutic effect or to have associated with it certain healing properties. Therapeutic oils contain active biologically occurring molecules and, upon topical application, exert a therapeutic effect. Non limiting examples include manuka oil, rosehip oil, which contains retinoids and is known to reduce acne and post-acne scars, and tea tree oil, which possesses anti-microbial activity including antibacterial, antifungal and antiviral properties as well as any other therapeutically beneficial oil known in the art of herbal medication. Many essential oils are considered "therapeutic oils." Other non limiting examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla and verbena.

Some embodiments include silicone oils. Non-limiting examples of silicone oils include a cyclomethicone, dimethicone, a polyalkyl siloxane, a polyaryl siloxane, a polyalkylaryl siloxane, a polyether siloxane copolymer, a poly (dimethylsiloxane)-(diphenyl-siloxane) copolymer, a dimethyl polysiloxane, an epoxy-modified silicone oil, a fatty acid-modified silicone oil, a fluoro group-modified silicone oil, a methylphenylpolysiloxane, phenyl trimethicone and a polyether group-modified silicone oil. In some embodiments, the silicone oil is cyclomethicone, cyclotetrasiloxane, cyclohexasiloxane, phyenyltrimethicone, Dow corning 246 Fluid (d6+d5) (cyclohexasiloxane & cyclopentasiloxane), Dow Corning 244 Fluid (cyclotetrasiloxane), Cyclomethicone 5-NF (cyclopentasiloxane), stearyl dimethicone, phenyltrimethicone, cetyl dimethicone, caprylyl methicone, PEG/PPG 18/18 dimethicone, or dimethiconol.

In one or more embodiments, the hydrophobic solvent may be selected from capric/caprylic triglycerides, cyclomethicone; isopropyl myristate, isopropyl palmitate, PPG-15 stearyl ether; octyldodecanol; isohexadecanol, diisopropyl adipate; cetearyl octanoate; MCT oil; heavy mineral oil; light mineral oil; coconut oil and soybean oil.

Mixtures of two or more hydrophobic solvents in the same foamable composition is contemplated. Furthermore, in certain embodiments, the use of mixtures of two or more hydrophobic solvents is preferred.

Yet, in certain embodiments, the hydrophobic solvent is a mixture of one or more liquid hydrophobic solvents, as listed above, together with an additional hydrophobic substance, which is not liquid (such as petrolatum), provided that the resultant mixture of all hydrophobic substances, is liquid at ambient temperature. In an embodiment the resultant mixture upon including propellant is liquid at ambient temperature. In certain embodiments the main hydrophobic substance in the formulation is a petrolatum, which is a semi solid, in combination with at least one liquid hydrophobic solvent. For example petrolatum may be added to provide a degree of occlusivity so that the formulation when applied to a skin surface can operate to increase skin moisture and or reduced transdermal water loss. In certain other embodiments a liquid hydrophobic solvent is not added. Fluidity of the composition can be achieved by utilizing liquidizing solvents (e.g. C12 C15 Alkyl benzoate) and or liquefied propellants and or optionally liquid adjuvants. Inclusion of higher amounts of propellant was found useful in order to improve flowability of the formulation from the canister or by using propellants having a higher vapor pressure.

Fatty Alcohol

If at all present, the fatty alcohol is selected from the group consisting of fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), tetracosanol, hexacosanol, octacosanol, triacontanol, tetratriacontanol, 1-triacontanol (C30), as well as alcohols with longer carbon chains (up to C50). In one or more other embodiments, the fatty alcohol is selected from the group consisting of fatty alcohols having 14 or less carbons in their carbon chain, such as lauryl alcohol and myristyl alcohol. In an embodiment the fatty alcohol is a solid at room temperature.

Fatty Acid

If at all present the fatty acid can have 16 or more carbons in its carbon chain, such as hexadecanoic acid (C16), heptadecanoic acid, stearic acid (C18), arachidic acid (C20), behenic acid (C22), tetracosanoic acid (C24), hexacosanoic acid (C26, heptacosanoic acid (C27), octacosanoic acid (C28), triacontanoic acid, dotriacontanoic acid, tritriacontanoic acid, tetratriacontanoic acid and pentatriacontanoic acid. as well as fatty acids with longer carbon chains (up to C50), or mixtures thereof. In one or more other embodiments, the fatty acid is selected from the group consisting of fatty alcohols having 14 or less carbons in their carbon chain, such as dodecanoic acid, myristic acid, myristoleic acid, and lauric acid. In an embodiment the fatty acid is a solid at room temperature.

Waxes

The foaming agent includes a wax. The wax which usually acts as a type of foam adjuvant is included in the foamable compositions to evolve the foaming property of the composition and/or to stabilize the foam. Wax refers to paraffin wax or beeswax or hydrogenated castor oil or another substance with similar properties. The term wax refers to a class of substances with properties similar to beeswax, in respect of (i) plastic behavior at normal ambient temperatures, a melting point above approximately 45° C., (ii) a relatively low viscosity when melted (unlike many plastics); and (iii) hydrophobic nature. Suitable exemplary waxes which can be incorporated into the formulation include animal, vegetable, mineral or silicone based waxes which may be natural or synthetic such as, for example: beeswax, Chinese wax, lanolin (wool wax), shellac wax, bayberry wax, candelilla wax, carnauba wax, castor wax, esparto wax, japan wax, ouricury wax, rice bran wax, soy wax, hydrogenated oil such ashydrogenated castor oil, hydrogenated cottonseed oil, or hydrogenated jojoba oil, mink wax, motan wax, ouricury wax, ozokerite, PEG-6 beeswax, rezowax, spent grain wax, stearyl dimethicone, paraffin waxes, such as paraffin 42-44, 51-53 58-62 wax, and the like and mixtures thereof. In one or more embodiments the wax is selected from a list comprising of a solid wax, an animal wax, a vegetable wax, a mineral wax, a natural wax or a synthetic wax. In certain embodiments the term wax can extend to hydrogenated oils. In one or more preferred embodiments, the wax is a beeswax or hydrogenated castor oil.

In one or more embodiments the range of ratio of wax/hydrophobic solvent can be about 100:1 to about 1:100; or about 90:1 to about 1:45; or about 80:1 to about 1:40; or about 70:1 to about 1:35; or about 60:1 to about 1:30; or about 50:1 to about 1:25; or about 40:1 to about 1:20; or about 30:1 to about 1:15; or about 20:1 to about 1:10; or about 15:1 to about 1:5; or about 10:1 to about 1:1; or any ranges in between such as 1:20 to 20:1, or preferably from 1:15 to 15:1. Preferably the range of the ratio of wax/hydrophobic solvent can be selected from a list comprising of: about 1:10; about 10:1; about 1:9 to about 9:1; or about 1:7 to about 7:1; or about 3:17 to about 17:3; or about 1:4 to about 4:1; or about 1:3 to about 3:1; or about 2:5 to about 5:2; or about 3:7 to about 7:3; or about 1:2 to about 2:1; or about 5:9 to about 9:5; or about 2:3 to about 3:2; or about 9:11 to about 11:9;

In one or more embodiments Shea butter may be further added to the composition. Shea butter may, for example, be used in addition to paraffin wax or bees wax or hydrogenated caster oil in order to enhance foam quality or to complement the action of one or more of them.

In one or more embodiments the foaming agent can further include be a fatty alcohol and shea butter, or a fatty acid and shea butter or a combination of a fatty alcohol and a fatty acid and shea butter.

Propellant

The composition requires the addition of a propellant in order to generate a foam.

Suitable propellants include volatile hydrocarbons such as butane, propane, isobutene or mixtures thereof. In one or more embodiments a hydrocarbon mixture AP-70 is used. In one or more other embodiments a lower pressure hydrocarbon mixture AP-46 is used. Both contain butane, propane, isobutene although in different proportions. AP-70 is composed of about 50% w/w of propane, about 20% w/w of isobutane and about 30% w/w of propane. AP-46 is composed of about 16% w/w of propane, about 82% w/w of isobutane and about 2% w/w of propane. Hydro fluorocarbon (HFC) propellants are also suitable as propellants in the context disclosed herein. Exemplary HFC propellants include 1,1,1,2 tetrafluorethane (Dymel 134), and 1,1,1,2,3, 3,3 heptafluoropropane (Dymel 227). Dimethyl ether is also useful. In one or more embodiments use of compressed gases (e.g., air, carbon dioxide, nitrous oxide, and nitrogen) is also possible.

In one or more embodiments a combination of at least two propellants, selected from HFC, hydrocarbon propellants, dimethyl ether and compressed gases is contemplated.

Yet, in additional embodiments, the propellant is a self-foaming propellant, i.e., a volatile liquid having a boiling point of less than the temperature of the target treatment site (such as the skin). An example of a post-foaming propellant is isopentane (bp=26° C.)

Any concentration of the propellant, which affords an acceptable foam, is useful in accordance with the present invention. In certain embodiments the propellant makes up between about 1% and about 30% of the foamable composition, or about 3% and 25%; and in certain preferred embodiments between about 5% and about 16% of the composition. In preparing the formulations the ingredients other than propellant are combined to 100% and the propellant is added thereafter so that the ratio of formulation to propellant can range from 100:1 to 100:30; 100:4 to 100:25 or preferably 100:5 to 100:16. Yet, in additional embodiments, the ratio of composition other than propellant to propellant is between about 100:20 and about 100:50.

Due to environmental concerns, as well as compatibility considerations, propellants that are not environmentally friendly are in one or more embodiments to be avoided. So chlorofluoro carbons (CFC's), which are known to damage the ozone layer in the atmosphere, are essentially excluded from the formulations.

In one or more embodiments, the propellant can also be used to expel formulation using a bag in can system or a can in can system as will be appreciated by someone skilled in the art. In certain embodiments the part of the propellant system is in the formulation and part separate from the formulation. In this way it is possible to reduce the amount of surfactant in the formulation but still provide good expulsion from the canister, where the foamable formulation is expelled quickly but without jetting or noise.

In one or more embodiments a foam formulation is expelled from a standard pressurized canister where the propellant is part of formulation. Formulations can be expelled or helped to be expelled by using propellant which is separate from the formulation using a bag in can or can in can system. Although, these systems can be used with compressed air the pressure may not be sufficient to expel the formulation through the device and higher pressure propellant such as AP70 should be selected. In one or more embodiments, the formulation is packaged in bag in can systems or in can in can system. In one or more embodiments, the formulation is expelled from the canister using the pressure provided by the propellant mixed with the formulation. In one or more embodiments, the formulation is expelled from the canister using the pressure provided by the propellant stored in a compartment surrounding the formulation. According to other embodiments part of the propellant system is in the formulation and part of the propellant system is separate from the formulation, which is used to expel said formulation using a bag or can in can system. In this way it is possible to reduce the amount of propellant within the formulation and avoid unwanted gaseous effects, for example in vaginal applications, but still provide good expulsion from the canister, where the foamable formulation is expelled sufficiently quickly but without jetting or noise. So by way of example, between about 1% to 3%; or between about 2% to 4%; between about 3% to 5% propellant (ratio of formulation to propellant of 100:1 to 3; 100:2 to 4; 100:3 to 5; respectively) is part of the formulation and a further amount of propellant is separate form the formulation and helps expel the formulation. In one or more embodiments a similar amount of propellant is in the formulation and a pump or other mechanical means is used to provide the additional expulsion force.

Modulating Agent

In one or more embodiments the modulating agent is used in a waterless composition which is surfactant and adjuvant free. The term modulating agent is used to describe an agent which can improve the stability of or stabilize a carrier or a foamable composition and/or an active agent by modulating the effect of a substance or residue present in the carrier or composition. The substance or residue may, for example, be acidic or basic or buffer system (or combinations thereof) and potentially alter an artificial pH in a waterless or substantially non-aqueous environment, such as, by acting to modulate the ionic or polar characteristics and any acidity or basesity balance of a waterless or substantially non-aqueous carrier, composition, foamable carrier or foamable composition or resultant foam or it may be a chelating or sequestering or complexing agent or it may be one or more metal ions which may act as a potential catalyst in a waterless or substantially non-aqueous environment or it may be an ionization agent or it may be an oxidizing agent.

In an embodiment, the modulating or additional component is a pH adjusting agent or a buffering agent and can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions such as EDTA or other such pharmaceutically or cosmetically acceptable.

Modulating agents may be added to the compositions of the subject invention, preferably from about 0.1% to about 10%, more preferably from about 1% to about 5%, of the composition. Where the active agent itself is the modulating agent alone or in combination with another modulating agent it will be added at an effective dose which may be outside these ranges. For example azaleic acid may be at about 15% of the composition. In an embodiment sufficient modulating agent is added to achieve an artificial pH in which the active agent is preferably stable. Such artificial pH may be acidic, maybe basic or may be neutral Further detail regarding modulating agents is found in co-pending Published U.S. Patent Application 2008/0206159, which is hereby incorporated in its entirety by reference.

The modulating agent to the foamable composition is useful for stabilizing pharmaceutical and cosmetic active agents which are unstable in certain pH conditions. It is known, for example, that active agents, which contain ester bond in their structure, tend to undergo hydrolysis of the ester bond at basic pH levels. Therefore, the addition of an agent, avoids the formation of basic pH condition, and thus, prevents degradation of such active agents. Many steroid compounds are known to undergo rearrangement at high pH, and again, adding an acidic modulating agent helps prevent such degradation. Another example of a pH-sensitive active agent is vitamin D, which degrades at low pH levels. In such a case, the addition of a basic modulating agent, such as triethanolamine is useful to maintain acceptable stability of this active agent.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since better protection against vaginal infection is attained in pH lower than 4.

In one or more embodiments, the modulating agent may also be a preservative or an antioxidant or an ionization agent. Any preservative, antioxidant or ionization agents suitable for pharmaceutical or cosmetic application may be used. Non-limiting examples of antioxidants are tocopherol, tocopherol succinate, ascorbic acid (vitamin C) and its salts, propyl galate, butylated hydroxy toluene and butyl hydroxy anisol. Non-limiting examples of positive ionization agents are benzyl conium chloride, and cetyl pyridium chloride. Non-limiting examples of negative ionization agents are sodium lauryl sulphate, sodium lauryl lactylate and phospholipids. In one or more embodiments the modulating agent is a flavonoid for example quercitin and/or rutin.

A safe and effective amount of an anti-oxidant/radical scavenger may be added to the compositions of the subject invention, preferably from about 0.1% to about 10%, more preferably from about 1% to about 5%, of the composition.

In one or more embodiments the modulating agent used is compatible with the active ingredient(s).

Ophthalmic Excipients

In one or more embodiments the formulation may comprise excipients that are suitable for ophthalmic use. By virtue of their suitability for ophthalmic use they may in certain embodiments be applicable on other sensitive targets such as for use internal and or external wounds or burns or in body cavities. Excipients selected as part of a drug carrier that can be used with the active pharmaceutical ingredients are identified by compatibility studies with active ingredients to ascertain which are compatible for use with the active pharmaceutical ingredients, for example, by examining which do not react with and or promote break down of the active pharmaceutical ingredients.

Not all excipients are appropriate for opthlmic use. Some may not be approved and require additional studies to achieve regulatory approval. Some may be eliminated as incompatible with the active ingredient and some may be eliminated agents because of physical considerations (e.g. as indicated below). Some may have or require that an effect be modified by the addition of other ingredients (e.g. such as rheology modifiers).

Oleaginous ointments are viscous preparations, which remain viscous when applied to the skin or other body surfaces; and they require extensive rubbing. Because of their viscosity, eye ointments cause blurred vision and consequent low tolerability, especially for long term treatment. Because of their high viscosity, drugs are trapped in the vehicle and cannot migrate through to their target site of action, for example, the skin or the eye.

Liquid, non viscous oleaginous medications are also disadvantageous, as they spill easily and thus, are very inconvenient to use. In eye treatment, liquid drops are difficult to apply and they require lying on the back at rest for accurate administration. Furthermore, because of their low viscosity, liquid oil vehicles cannot carry suspended drugs, which tend to precipitate and if the viscosity is not high enough, thereby impairing the uniformity of the therapeutic product.

In one or more embodiments the formulations are not highly viscous. In one or more other embodiments the formulations do not provide low viscosity. In one or more embodiments the formulations are thixotropic so that on application of shear force their viscosity decreases and they become more flowable. On one or more embodiments the formulations are foams which are breakable on shear force. In one or more embodiments the foams are based on thixotropic gel formulations. In one or more embodiments the viscosity of the formulation prior to addition of propellant is more than about 1000 cps and less than about 25,000 cps.

Additional Components

In an embodiment, a composition disclosed herein includes one or more additional components. Such additional components include but are not limited to anti perspirants, anti-static agents, bulking agents, cleansers, colorants, skin conditioners, deodorants, diluents, dyes, fragrances, hair conditioners, herbal extracts, humectants, keratolytic agents, modulating agents, pearlescent aids, perfuming agents, pH modifying or stabilizing agents, skin penetration or permeation enhancers, softeners, solubilizers, sunscreens, sun blocking agents, sunless tanning agents, viscosity modifiers, flavanoids and vitamins. As is known to one skilled in the art, in some instances a specific additional component may have more than one activity, function or effect.

In certain embodiments, the additional component is an oil soluble preservative, or an oil soluble antioxidant, or an oil soluble radical scavenger, or an oil soluble complexing agent, or an oil soluble pigment or dye.

Definitions

All % values are provided on a weight (w/w) basis.

By the term "about" herein it is meant that a figure or range of figures can vary plus or minus up to 30%. So in this embodiment if a figure of "about 1" is provided then the amount can be up to 1.3 or from 0.70. In other embodiments it can reflect a variation of plus or minus 20%. In still further embodiments it can describe a variation of plus or minus 10%. In still further embodiments it can describe a variation of plus or minus 5%. As will be appreciated by one of the art there is some reasonable flexibility in formulating compositions such that where one or more ingredients are varied successful formulations may still be made even if an amount falls slightly outside the range. Therefore, to allow for this possibility amounts are qualified by about. In one or more other embodiments the figures may be read without the prefix about.

The term "waterless," as used herein, means that the composition contains no, or substantially no, free or unassociated or absorbed water. Similarly, "waterless" or "substantially waterless" carriers contain at most incidental and trace amounts of water.

By the term "single phase" herein it is meant that after addition of propellant to the composition or carrier, the liquid components of the foamable composition or carrier are fully miscible, and the solid components if any, are either dissolved or suspended in the composition. By substantially a single phase is meant that the composition or carrier after addition of propellant is primarily or essentially a single phase as explained above, but may also have present a small amount of material which is capable of forming or may form a separate phase amounting to less than about 5% of the composition or carrier after the addition of propellant, preferably less than about 3%, and more preferably less than about 1%.

The term "unstable active agent" as used herein, means an active agent which is oxidized and/or degraded within less than a day, and in some cases, in less than an hour upon exposure to air, light, skin or water under ambient conditions.

The term "co-surfactant" as used herein, means a molecule which on its own is not able to form and stabilize satisfactorily an oil in water emulsion but when used in combination with a surfactant the co-surfactant has properties, which can allow it to help surfactants to create an emulsion and can boost the stabilizing power or effect of the surfactant and can include, for example, a fatty alcohol, such as cetyl alcohol or a fatty acid such as stearic acid. Cetyl alcohol is a waxy hydrophobic substance that can be emulsified with water using a surfactant. Some substances may have more than one function and for example, fatty alcohols can in some formulations act as a co-solvent. In certain circumstances a co-surfactant can itself be converted in to a surfactant or soap by, for example, adding a base, such as, triethanolamine to a fatty acid like stearic acid.

The identification of a "polyol", as used herein, is an organic substance that contains at least two hydroxy groups in its molecular structure.

In one or more embodiments, the polyol is a diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polyol is a triol (a compound that contains three hydroxy groups in its molecular structure), such as glycerin, butane-1,2,3-triol, butane-1,2,4-triol and hexane-1,2,6-triol.

In one or more embodiments, the polyol is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

In one or more embodiments, the polyol is a sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol.)

Mixtures of polyols, including (1) at least one polyol selected from a diol and a triol; and (2) a saccharide are contemplated within the scope of the present disclosure.

According to some embodiments, the composition is polyol-free i.e., free of polyols. In other embodiments, the composition is substantially free and comprises less than about 5% final concentration of polyols, preferably less than 2%, more preferably less than 1%. Where a formulation includes insignificant amounts of polyols it is considered to be essentially free of them.

In an embodiment, the polyol is linked to a hydrophobic moiety. In the context of the present disclosure, a polyol linked to a hydrophobic moiety is still defined as a "polyol" as long as it still contains two or more free hydroxyl groups.

In an embodiment, the polyol is linked to a hydrophilic moiety. In the context of the present disclosure, a polyol linked to a hydrophilic moiety is still defined "polyol" as long as it still contains two or more free hydroxyl groups.

The term "water activity" as used herein, activity represents the hydroscopic nature of a substance; or the tendency of a substance that absorbs water from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Every microorganism has a limiting Aw, below which it will not grow; e.g., for *Streptococci, Klebsiella* spp, *Escherichia coli, Clostridium perfringens*, and *Pseudomonas* spp, the Aw value is 0.95. *Staphylococcus aureus* is most resistant and can proliferate with an Aw as low as 0.86, and fungi can survive at Aw of at least 0.7. In one or more embodiments, the concentration of the hydrophobic solvent, and/or foaming agent in the composition is selected to provide an Aw value selected from the ranges of (1) about 0.8 and about 0.9; (2) about 0.7 and about 0.8; and (3) less than about 0.7. Delivering the formulation in a pressurized package does not allow for humidity to be absorbed by the preparation, and therefore, the water free character of the composition cannot be damaged.

In an embodiment no preservative is added because the formulation is a waterless hydrophobic solvent or oil-based formulation having an Aw (Water Activity) value of less than 0.9, less, or less than about 0.8, or less than about 0.7 or less than about 0.6 and preferably less than about 0.5 which is below the level of microbial proliferation.

In one or more embodiments, the hydrophobic carrier composition further contains an anti-infective agent, selected from the group of an antibiotic agent, an antibacterial agent, an antifungal agent, an agent that controls yeast, an antiviral agent and an antiparasitic agent. In a preferred embodiment the anti infective agent comprises a tricyclic antibiotic. Not only can combining the anti-infective effect of a hydrophobic carrier composition, with an anti-infective agent can result in a synergistic effect and consequently higher success rate of the treatment but the combination with the foaming agent achieves a formulation which is physically stable as demonstrated herein in the Examples. Moreover the use of hydrophobic based water free formulation can maximize the antimicrobial potential of the formulations. Storage in sealed, light and airtight canisters can assist in preserving the formulations.

The identification of a "solvent," as used herein, is not intended to characterize the solubilization capabilities of the solvent for any specific active agent or any other component of the foamable composition. Rather, such information is provided to aid in the identification of materials suitable for use as a part in the foamable carriers described herein.

Substantially Alcohol Free

Lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the composition is substantially alcohol-free i.e., free of short chain alcohols. In other embodiments, the composition comprises less than about 5% final concentration of lower alcohols, preferably less than 2%, more preferably less than 1%. Where a formulation contains insignificant amounts of short chain alcohols it is considered to be essentially free of them.

Substantially Surfactant Free

Surfactants have been categorized in to various sub classes depending on their ionic characteristics, namely non-ionic surfactants, anionic, cationic, zwitterionic, amphoteric and amphiphilic surfactants. The term surfactant has been often loosely used in the art to include substances which do not function effectively as stand alone surfactants to reduce surface tension between two substances or phases. Reduction of surface tension can be significant in foam technology in relation to the ability to create small stable bubbles. For example fatty alcohols, fatty acids and certain waxes are amphiphatic, are essentially hydrophobic with a minor hydrophilic region and for the purposes of forming an emulsion they are usually regarded as an oil and thus have a "required" HLB value" for the purpose of determining what standard surfactant might be appropriate to use with the oil phase. However unlike standard or customary surfactants, these substances are not effective as stand-alone surfactants in foamable emulsion compositions, because of their very weak emulsifying capacity and further due to their weak foaming capacity on their own. They are occasionally used in a supporting role as co-emulsifiers, i.e., in combination with a standard surfactant but are commonly used as thickeners and have successfully been used as foam adjuvants to assist customary surfactants to boost foam quality and stability. For clarification, in the context herein, the term "standard surfactant" or "customary surfactant" refers herein to customary non-ionic, anionic, cationic, zwitterionic, amphoteric and amphiphilic surfactants. A fatty alcohol or a fatty acid and certain waxes are not regarded as a standard surfactant. However, in contrast, an ether or an ester formed from such fatty alcohols or fatty acids can be regarded as a customary surfactant.

Generally, surfactants are known to possess irritation potential. One way that is used to try and reduce potential irritation and drying of the skin or mucosa due to surfactants and their repeated use especially when formulations are to be left on the skin or mucosa rather than being washed off is to use essentially or primarily non ionic surfactants at preferably low concentrations below 5%. The current breakthrough of identifying formulations which produce quality breakable foam yet omitting customary surfactants from a composition may contribute to improved tolerability of such a composition and can be an important advantage. This is especially so when a formulation is to be applied to a very sensitive target site, and particularly so on a repeated basis.

Non-limiting examples of classes of customary non-ionic surfactants include: (i) polyoxyethylene sorbitan esters (polysorbates), such as polysorbate 20, polysorbate 40, polysorbate 60 and polysorbate 80; (ii) sorbitan esters, such as sorbitan monostearate sorbitan monolaurate and sorbitan monooleate; (iii) polyoxyethylene fatty acid esters, such as PEG-8 stearate, PEG-20 stearate, PEG-40 stearate, PEG-100 stearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters, such as PEG-150 distearate, (v) polyethylene glycol (PEG) ethers of fatty alcohols, such as; (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides; (xi) sugar esters (mono-, di- and tri-esters of sucrose with fatty acids) and (xii) polyethylene glycol alkyl phenols.

In certain embodiments, the composition is free of customary surfactants, or "surfactant-free" and in certain embodiments the foamable composition is substantially free of customary surfactants, or "substantially surfactant-free".

In the context herein, the term "substantially surfactant-free composition" relates to a composition that contains a total of less than about 0.4% of a surfactant selected from the group consisting of customary non-ionic, anionic, cationic, zwitterionic, amphoteric and ampholytic surfactants. Preferably, the composition comprises less than about 0.3% or less than about 0.2% by weight of a standard surfactant and more preferably less than about 0.1%. Where a formulation includes insignificant amounts of surfactants it is considered to be essentially free of them.

Non-surfactant or surfactant-free compositions will comprise no or negligible levels of surface active agents.

In additional embodiments, the term "substantially surfactant-free" relates to a composition wherein the ratio between the foaming agent and the surfactant is between 50:1 or 20:1; or between 20:1 and 10:1 or between 100:1 and 20:1.

In certain embodiments, the composition is free or substantially free of an ionic surfactant. In certain embodiments, the composition is free or substantially free of a non-ionic surfactant.

Substantially Polymer-Free

By the term polymeric agent it is intended to mean a compound having multiple repeated units such as cellulose polymers, acrylic polymers, block polymers and copolymers. In one or more certain embodiments the polymeric agent has a molecular weight of in excess of a 1000 Daltons. In one or more embodiments the formulations are substantially polymer free. In one or more embodiments the formulations are substantially polymer free of a polymeric agent selected from the group consisting of a bioadhesive agent, a gelling agent, a film forming agent and a phase change agent, being locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers, semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxycthylcellulose, and cationic celluloses, carbomer (homopolymer of acrylic acid is crosslinked with an allyl ether pentaerythritol, an allyl ether of sucrose, or an allyl ether of propylene); poloxamers (synthetic block copolymer of ethylene oxide and propylene); polyethylene glycol having molecular weight of 1000 or more (e.g., PEG 1,000, PEG 4,000, PEG 6,000 and PEG 10,000) and which could function as a hydro alcoholic foam booster. By substantially polymer free it is intended to mean less than about 5%, preferably less than about 2%. By essentially polymer free it is intended to mean less than about 1%, preferably less than about 0.5%. In further embodiments they are essentially polymer free and in still further embodiments they are free of polymeric agents.

In alternative embodiments the formulations may comprise a polymeric agent in such case the polymeric agents are oil soluble polymeric agents. Non limiting examples of oil-soluble polymeric agents are: Ethyl cellulose, alkylated guar gum, trimethylsiloxysilicate, alkyl-modified silicone, polyamide-modified silicone, homopolymers and copolymers of alkyl methacrylates, alkyl acrylates, and alkyl styrenes polyisobutene, polybutyl metacrylate, polycyclohexylstyrene.

According to one or more embodiments, the composition comprises less than about 0.1% by weight of a polymeric agent and more preferably less than about 0.05%. t Polymer-free compositions will comprise no or negligible levels of polymeric agents.

In the art, the term polymeric agent can be used loosely to refer to any polymer. However, in some embodiments polymers that do not have a gel building role but may act in other ways are not excluded from the compositions. In one or more embodiments a polyether siloxane copolymer and a poly(dimethylsiloxane)-(diphenyl-siloxane) copolymer and the like, which can provide a good feeling to the composition are not excluded.

Physical Characteristics of the Foamable Composition and Foam

A foamable composition manufactured according to one or more embodiments herein is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

In one or more embodiments the foamable composition is a single phase solution. In one or more embodiments the foamable composition is substantially a single phase solution. In certain circumstances, where the active agent is insoluble and is presented as a homogenous suspension, the formulation is turbid or cloudy.

In one or more embodiments the foam composition has an acceptable shelf-life of at least six months or at least nine months or at least one year, or of at least about one and a half years or at least two years at ambient temperature. A feature of a product for cosmetic or medical use is long term stability. Propellants, which are a mixture of low molecular weight hydrocarbons, tend to impair the stability. The foamable compositions herein are surprisingly stable, even in the absence of customary surfactants and or foam adjuvants. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing a substantial amount of semi-solid hydrophobic solvents, e.g., white petrolatum, as the main ingredients of the oil phase of the emulsion, will likely exhibit high viscosity and poor flowability and can be inappropriate candidates for a foamable composition. Thus in one or more embodiments semi-solid hydrophobic solvents are a subsidiary component in the composition, for example being present at less than about 25%, less than about 20%, less than about 15%, less than about 10%, or less than about 5% by weight of the foamable composition. In other embodiments they can be present in higher amounts due to the solvent effect of the propellant diluting the formulation and enabling flowability or where the formulation is presented as a gel or ointment.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of a more stable foam, which does not collapse spontaneously immediately upon discharge from the container. The finer foam structure looks and feels smoother, thus increasing its usability and appeal.

Foam Density

Another property of the foam is specific gravity or density, as measured upon release from the aerosol can. Typically, foams have specific gravity of less than 0.50 g/mL or less than 0.12 g/mL, depending on their composition and on the propellant concentration. In one or more embodiments the foam density is about less than 0.3 g/mL or is about less than 0.2 g/mL; or is about less than 0.1 g/mL or is about less than 0.05 g/mL.

Shakability

'Shakability' means that the composition contains some or sufficient flow to allow the composition to be mixed or remixed on shaking. That is, it has fluid or semi fluid properties. Shakability is described further in examples in Tests section. In one or more certain limited embodiments the formulation is poorly shakable but is nevertheless flowable.

Breakability/Collapse Time

A further aspect of the foam is breakability. The balance between stability and breakability of the foam coming out of the container is very delicate: on the one hand the foam should preferably not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The breakable foam is thermally stable, yet breaks under shear force. Shear-force breakability of the foam is clearly advantageous over thermally-induced breakability. Thermally sensitive foams start to collapse immediately upon exposure to skin temperature and, therefore, cannot be applied on the hand and afterwards delivered to the afflicted area.

The collapse time of foam represents its tendency to be temperature-sensitive and its ability to be at least stable in the short term so as to allow a user sufficient time to comfortably handle and apply the foam to a target area without being rushed and or concerned that it may rapidly collapse, liquefy and or disappear. Collapse time, as an indicator of thermal sensitivity, is examined by dispensing a given quantity of foam and photographing sequentially its appearance with time during incubation at 36° C. (the procedure is explained in further detail in the Examples). The collapse time result is defined as the time when the foam reaches 50% of its initial height. Foams which are structurally stable on the skin and have not reached 50% of their initial height after at least one minute are termed "short term stable" carriers or foams. Simple collapse time can be measured by applying a foam sample on a body surface like the fingers at normal body temperature of about 37° C.

Oils may cause foam to be thermolabile and "quick breaking." However, in certain embodiments herein, despite the presence of high oil content, quite unexpectedly the foam is substantially thermally stable. By "substantially thermally stable" it is meant that the foam upon application onto a warm skin or body surface at about 35-37° C. it does not collapse within about 30 seconds. Thus, in one or more embodiments the simple collapse time of the foam is more than about 30 seconds or more than about one minute or more than about two minutes. In one or more limited embodiments simple collapse time can be a little shorter than 30 seconds, but not less than about 20 seconds. In one or further or alternative embodiments the collapse time is measured by introducing a sample of foam into an incubator at 36° C. and the collapse time of the foam is more than 30 seconds or more than about one minute or more than about two minutes.

Pharmaceutical Composition

The foamable oleaginous composition of the present invention can be used by itself as a topical treatment of a body surface, as many hydrophobic solvents such as emollients, unsaturated oils, essential oils or therapeutic oils that possess cosmetic or medical beneficial effects. Furthermore, it is an ideal vehicle for active pharmaceutical ingredients and active cosmetic ingredients. In the context active pharmaceutical ingredients and active cosmetic ingredients are collectively termed "active agent" or "active agents". The absence of surfactants in the composition is especially advantageous, since no surfactant-related adverse reactions are expected from such a composition. Some surfactants may act to facilitate gelling of the pre-foam formulation. The absence of such surfactants may avoid this undesirable phenomenon. In one or more embodiments the active agent is soluble in the composition of a phase thereof. In one or more other embodiments it is partially soluble or insoluble. When partially soluble or insoluble the active agent is presented as a suspension or it can be encapsulated in a carrier.

Whilst some active ingredients are effectively inert in the wax/solvent compositions described herein other active ingredients are very sensitive to degradation and can react, break down or rearrange readily. For example, tetracycline antibiotics such as minocycline or doxycycline break down upon being exposed to many excipients as disclosed in the study described in Example 9. Thus, in one or more embodiments an active agent is first tested for compatibility with each of the formulation ingredients. In one or more embodiments the active agent is compatible with the other ingredients.

Suitable active agents include but are not limited to an active herbal extract, an acaricides, an age spot and keratose removing agent, an allergen, an alpha hydroxyl acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an antiinfective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, a beta-hydroxy acid, benzoyl peroxide, a cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a pesticide, a progesterone, a protein, a photodynamic therapy agent, a radical scavenger, a refatting agent, a retinoid, a sedative agent, a scabicide, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover. As is known to one skilled in the art, in some instances a specific active agent may have more than one activity, function or effect.

Encapsulation of an Active Agent

In one or more embodiments, the active agent is encapsulated in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the drug from degradation; (2) modification of the drug release rate from the composition; (3) control of skin penetration profile; and (4) mitigation of adverse effects, due to the controlled release of the active agent from the encapsulation particles.

Solubility of an Active Agent

Solubility of the steroid is an important factor in the development of a stable foamable composition according to the present invention.

For definition purposes, in the context of the present invention, the descriptive terminology for solubility according to the US Pharmacopoeia (USP 23, 1995, p. 10), the European Pharmacopoeia (EP, 5th Edition (2004), page 7) and several other textbooks used in the art of pharmaceutical sciences (see for example, Martindale, The Extra Pharmacopoeia, 30th Edition (1993), page xiv of the Preface; and Remington's Pharmaceutical Sciences, 18th Edition (1990), page 208) is adapted:

| Descriptive Term | Parts of Solvent Required for 1 Part of Solute |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble or Insoluble | 10,000 and over |

Thus, in one or more embodiments, the active agent is "soluble", "freely soluble" or "very soluble" (as defined above) in the composition. Yet, in certain cases, the active agent is "very slightly soluble", "slightly soluble" or "sparingly soluble" in the composition.

Yet, in one or more embodiments, the active agent is insoluble i.e., "requires 10,000 parts or more of a solvent to be solubilized", in the composition.

In certain embodiments it is desirable that the active agent is maximally soluble in the composition, because solubility of the active agents is expected to increase its bioavailability.

Yet, in additional embodiments it is desirable that the active agent is insoluble in the composition, because its degradation is enhanced when it is dissolved. In such cases, the hydrophobic solvent is selected by (1) testing the solubility of said active agent in various hydrophobic solvents, followed by (2) inclusion in the composition of such solvents that do not solubilize the active agent. In one or more embodiments the active agent is presented as a suspension. In one or more further embodiments the active agent is micronized, which can assist in delivery into the skin, mucosal membrane and body cavity surfaces and also aid homogenous distribution within the formulation.

Exemplary Groups of Active Agents
Antibiotics

In the context of the present disclosure, an antibiotic agent is a substance, that has the capacity to inhibit the growth of or to destroy bacteria and other microorganisms.

In one or more embodiments, the antibiotic agent is selected from the classes consisting beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, dicarboxylic acids, antibiotic metals including antibiotic metal ions, oxidizing agents, a periodate, a hypochlorite, a permanganate, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds including non classified antibiotic compound analogs, derivatives, salts, ions, complexes and mixtures thereof.

Tetracyclines

According to some embodiments, the antibiotic agent is a tetracycline. The tetracyclines (also referred to herein as "tetracycline antibiotics") are a group of antibacterials, originally derived from certain *Streptomyces* spp., having the same tetracyclic nucleus, naphthacene, and similar properties. They are usually bacteriostatic but act by interfering with protein synthesis in susceptible organisms. Tetracycline antibiotics are susceptible to degradation by oxidation.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Chlortetracycline, oxytetracycline, tetracycline, demeclocycline are all natural products that have been isolated from *Streptomyces* spp. The more recent tetracyclines, namely methacycline, doxycycline, and minocycline, are semisynthetic derivatives. Methacycline, like demeclocycline, has a longer half-life than tetracycline. Minocycline is active against some tetracycline-resistant bacteria, including strains of staphylococci. Both doxycycline and minocycline are more lipid-soluble than the other tetracyclines and they penetrate well into tissues. They are thus more suitable for incorporating into oily or emollient containing formulations. However, they have a place in the treatment of chlamydial infections, rickettsial infections such as typhus and the spotted fevers, mycoplasmal infections such as atypical pneumonia, pelvic inflammatory disease, Lyme disease, brucellosis, tularaemia, plague, cholera, periodontal disease, and acne. The tetracyclines have also been useful in the treatment of penicillin-allergic patients suffering from venereal diseases, actinomycosis, bronchitis, and leptospirosis. Minocycline may sometimes be used in multidrug regimens for leprosy. Doxycycline may be used for the treatment and prophylaxis of malaria; it is also used in the management of anthrax.

In an embodiment the active ingredient may be any one of the following non limiting examples chlortetracycline, demeclocycline, doxycycline, lymecycline, meclocycline, methacycline, minocycline, oxytetracycline, rolitetracycline, tetracycline. In a preferred embodiment they are doxycycline or minocycline.

Tetracycline antibiotics can be incorporated into the formulations of the present invention to treat, ameliorate or prevent a multitude of disorders responsive to tetracycline antibiotics. The formulations can be applied topically to the skin or to the genitals or to mucosal membranes and on and around the eye, sub-gingival and can be applied into a wide range of body cavities, including aural, digestive, oral, nasal, urethra, penal, endocervical, rectum, respiratory, and vaginal and tooth pocket. Non limiting examples of applications include eye infections, blepharitis, dry eye, inclusion conjunctivitis, glaucoma, inflammatory ocular conditions where bacterial infection or a risk of bacterial ocular infection exists, neuropathic atrophy (in diabetes), abrasions, injuries, wounds, burns, ulcers, pyoderma, furunculosis, granuloma inguinale, periodontitis, rosacea, post-operation infections and tissue reconstruction, trachoma, lymphogranuloma venereum, granuloma inquinale, acne, inflammation, sinusitis, neuro-protection, washing out, disinfection, and stabilization of body cavities, at on around or in the site of an operation, which for example can provide multiple therapeutic effects, such as, inhibition of post operation adhesions, anti infection, neuro-protection.

Whether delivered as a foam, gel, ointment or suspension the active pharmaceutical tetracycline can be present by weight in the range of about 0.2% to about 20%, or at about 0.2%, at about 0.3%, at about 0.4%, at about 0.5%, at about 0.6%, at about 0.7%, at about 0.8%, at about 0.9%, at about 1%, at about 1.5%, at about 2%, at about 2.5%, at about 3%, at about 3.5% at about 4%, at about 4.5%, at about 5%, at about 6%, at about 7%, at about 8%, at about 9%, at about 10%, at about 12%, or at about 14%, at about 16%, at about 18%, or at about 20%.

Tetracyclines and Skin Infections

Tetracyclines have been used in ophthalmic ointments for the prevention or treatment of infections of the eye caused by susceptible bacteria. Although minor skin infections and wounds usually heal without treatment, some minor skin wounds do not heal without therapy and it is impossible to determine at the time of injury which wounds will be self-healing. Therefore, some experts believe that, by reducing the number of superficial bacteria, topical anti-infectives are useful for preventing infection in minor skin injuries (e.g., cuts, scrapes, burns).

Tetracycline hydrochloride may be used topically in the treatment of inflammatory acne vulgaris. Tetracyclines are usually bacteriostatic in action, but may be bactericidal in high concentrations or against highly susceptible organisms.

Tetracyclines appear to inhibit protein synthesis in susceptible organisms primarily by reversibly binding to 30S ribosomal subunits, thereby inhibiting binding of aminoacyl transfer-RNA to those ribosomes. In addition, tetracyclines appear to reversibly bind to 50S ribosomal subunits. There is preliminary evidence that tetracyclines also alter cytoplasmic membranes of susceptible organisms resulting in leakage of nucleotides and other intracellular components from the cell. At high concentrations, tetracyclines also inhibit mammalian protein synthesis.

The exact mechanisms by which tetracyclines reduce lesions of acne vulgaris have not been fully elucidated; however, the effect appears to be partly the result of the antibacterial activity of the drugs. Following topical application to the skin of a 0.22% solution of tetracycline hydrochloride in a vehicle containing n-decyl methyl sulfoxide (Topicycline®; no longer commercially available in the US), the drug inhibits the growth of susceptible organisms (principally *Propionibacterium acnes*) on the surface of the skin and reduces the concentration of free fatty acids in sebum. The reduction in free fatty acids in sebum may be an indirect result of the inhibition of lipase-producing organisms which convert triglycerides into free fatty acids or may be a direct result of interference with lipase production in these organisms. Free fatty acids are comedogenic and are believed to be a possible cause of the inflammatory lesions (e.g., papules, pustules, nodules, cysts) of acne. However, other mechanisms also appear to be involved because clinical improvement of acne vulgaris with topical tetracyclines does not necessarily correspond with a reduction in the bacterial flora of the skin or a decrease in the free fatty acid content of sebum. (Martindale Electronic Version 2007).

Tetracyclines, Solubility and Stability

Tetracyclines are known to be unstable in the presence of water, as well as numerous types of formulation excipients, such as protic solvents, various surfactants and certain oils. We surprisingly discovered that the inclusion of tetracyclines in a composition comprising a hydrophobic solvent and a foaming agent described herein results in a stable product, with extended stability of the tetracycline. In an embodiment a hydrophobic solvent is selected by (1) testing the solubility of said active agent in various hydrophobic solvents, (2) identifying those that do not solubilize the active agent followed by (3) inclusion in the composition of such solvents that do not solubilize the active agent. In certain embodiments the tetracycline is insoluble in the composition.

Doxycycline

According to some embodiments, the tetracycline is doxycycline. Doxycycline is a tetracycline antibiotic and also has anti-inflammatory and immunomodulatory effects. Doxycycline is a semisynthetic tetracycline antibiotic derived from oxytetracycline. In addition to antimicrobial activity, the drug has anti-inflammatory and immunomodulatory effects. It is available as Doxycycline calcium, doxycycline hyclate and doxycycline monohydrate. Doxycycline hyclate and doxycycline monohydrate occur as yellow, crystalline powders. The hyclate is soluble in water and slightly soluble in alcohol; the monohydrate is very slightly soluble in water and sparingly soluble in alcohol. Doxycycline calcium is formed in situ during the manufacturing process. Following reconstitution of doxycycline hyclate powder for IV administration with sterile water for injection, solutions have a pH of 1.8-3.3.

The mechanism(s) by which doxycycline reduces inflammatory lesions (papules and pustules) in patients has not been elucidated, but these effects may result at least in part from the anti-inflammatory actions of the drug; other mechanisms may be involved Doxycycline is used for the treatment of rosacea treatment or prophylaxis of anthrax (including inhalational anthrax [postexposure]), treatment of presumed or confirmed rickettsial infections, including Rocky Mountain spotted fever (RMSF), fever, ehrlichiosis, and anaplasmosis, and for the treatment of *Bartonella* infections, for the treatment of brucellosis, for the treatment of *Burkholderia* Infections, *Chlamydial* Infections, Lymphogranuloma venereum Psittacosis, *Ehrlichiosis* and *Anaplasmosis, Gonorrhea* and Associated Infections, Epididymitis, Proctitis, *Granuloma Inguinale* (Donovanosis,) *Legionella* Infections, *Leptospirosis*, Lyme Disease, Prophylaxis of Lyme Disease, Erythema Migrans, Early Neurologic Lyme Disease, Lyme Carditis, or Borrelial Lymphocytoma, Lyme Arthritis, Malaria, and prevention, Mycobacterial Infections, *Mycobacterium marinum* Infections, Pelvic Inflammatory Disease, Parenteral Regimens, Plague, pleural Effusion, Rickettsial Infections, Q Fever, Syphilis, Tularemia, Treatment, Postexposure Prophylaxis When reconstituted and diluted with 0.9% sodium chloride or 5% dextrose, doxycycline hyclate IV solutions containing 0.1-1 mg of doxycycline per mL are stable for 48 hours at 25° C.; when reconstituted and diluted with Ringer's, 10% invert sugar, Normosol-M® in D5W, Normosol-R® in D5W, Plasma-Lyte® 56 in 5% dextrose, or Plasma-Lyte® 148 in 5% dextrose, doxycycline hyclate IV solutions containing 0.1-1 mg/mL are stable for 12 hours at room temperature. The manufacturer states that doxycycline hyclate solutions prepared with any of these infusion solutions are stable for 72 hours at 2-8° C. when protected from direct sunlight and artificial light; however, after storage in this manner, infusion of these solutions must be completed within 12 hours Doxycycline hyclate IV solutions diluted to a concentration of 0.1-1 mg/mL with lactated Ringer's injection or 5% dextrose in lactated Ringer's injection must be infused within 6 hours to ensure stability. During infusion, all doxycycline hyclate IV solutions must be protected from direct sunlight. (Martindale 2007 Electronic Version). Thus it can be seen that Doxycycline is not stable for more than short periods of a matter of hours.

Preparations of doxycycline hyclate have an acid pH and incompatibility may reasonably be expected with alkaline preparations or with drugs unstable at low pH.

Doxycycline is more active than tetracycline against many bacterial species including *Streptococcus pyogenes, enterococci, Nocardia* spp., and various anaerobes. Cross-resistance is common although some tetracycline-resistant *Staphylococcus aureus* respond to doxycycline. Doxycycline is also more active against protozoa, particularly *Plasmodium* spp.

Doxycycline is a tetracycline derivative with uses similar to those of tetracycline. It may sometimes be preferred to other tetracyclines in the treatment of susceptible infections because of its fairly reliable absorption and its long half-life that permits less frequent (often once daily) dosing. It also has the advantage that it can be given (with care) to patients with renal impairment. However, relatively high doses may need to be given for urinary-tract infections because of its low renal excretion.

For relapsing fever and louse-borne typhus, for the prophylaxis of leptospirosis, for periodontiti, for Lymphatic filariasis, for Musculoskeletal and joint disorders and for the treatment of acne.

Minocycline

According to some embodiments, the tetracycline is minocycline. Minocycline hydrochloride is a semisynthetic tetracycline antibiotic derived from tetracycline. The drug is usually bacteriostatic in action; it exerts its antimicrobial activity by inhibiting protein synthesis. It is a yellow crystalline powder that is sparingly soluble in water; slightly soluble in alcohol; practically insoluble in chloroform and in ether; soluble in solutions of alkali hydroxides and carbonates. pH of a solution in water containing the equivalent of minocycline 1% is between 3.5 and 4.5. Preparations of minocycline hydrochloride have an acid pH and incompatibility may reasonably be expected with alkaline preparations or with drugs unstable at low pH.

Minocycle is highly sensitive and should be stored in airtight containers and protected from light to prevent degradation. Therefore use in foamable formulations stored in airtight sealed containers under pressure with propellant may contribute to preserving stability subject to selection of compatible canisters and accessories.

Photosensitivity, manifested as an exaggerated sunburn reaction on areas of the body exposed to direct sunlight or ultraviolet light, has occurred with tetracyclines and Minocycline has been associated with pigmentation of the skin and other tissues.

Minocycline has a spectrum of activity and mode of action similar to that of tetracycline but it is more active against many species including *Staphylococcus aureus*, streptococci, *Neisseria meningitidis*, various enterobacteria, *Acinetobacter, Bacteroides, Haemophilus, Nocardia*, and some mycobacteria, including *M. leprae*. Partial cross-resistance exists between minocycline and other tetracyclines but some strains resistant to other drugs of the group remain sensitive to minocycline, perhaps because of better cell-wall penetration. Minocycline is a tetracycline derivative with uses similar to those of tetracycline. It is also a component of multidrug regimens for the treatment of leprosy and has been used in the prophylaxis of meningococcal infection to eliminate the carrier state, but the high incidence of vestibular disturbances means that it is not the drug of choice for the latter. It has neuroprotective properties. It is being investigated for motor neurone disease, for the management of Huntington's chorea. It is used in the treatment of rheumatoid arthritis and in the treatment of various skin disorders, including acne.

Steroids

In an embodiment, the active agent is a steroid. In certain embodiments the steroid is a corticosteroid, including but not limited to, hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

In certain embodiments, the steroid is a hormone or a vitamin, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, lanosterol, prednisolone, prednisone, progesterone, spironolactone, timobesone and testosterone, as well as analogs, derivatives, salts, ions and complexes thereof. For substances like calcitriol, very low amounts such as about 0.0001% to about 0.005% by weight of foam formulation or gel or ointment or suspension, or about 0.0001%, about 0.0002%, about 0.0003%, about 0.0004%, about 0.0005%, about 0.0006%, about 0.0007%, about 0.0008%, about 0.0009%, about 0.001%, about 0.0011%, about 0.0012%, about 0.0013%, about 0.0014%, about 0.0015%, about 0.0016%, about 0.0017%, about 0.0018%, about 0.0019%, about 0.002%, about 0.003%, about 0.004%, about 0.005% by weight are effective. In some embodiments the active pharmaceutical agent is delivered by more than one route, for example, topically and body cavity.

In an embodiment, the steroid is mometasone furoate. In certain embodiments it can be used topically to treat psoriasis and dermatitis. In certain other embodiments it can be applied in nasal administration to treat disorders, such as, allergic rhinitis and asthma.

NSAID

In an embodiment, the active agent is a non-steroidal anti-inflammatory agent. In the context a nonsteroidal anti-inflammatory agent (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is pro-inflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

Local Anesthetic Agents

In an embodiment, the active agent is a local anesthetic agent. Without limiting the scope, the anesthetic agent can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated.

Keratolytically Active Agents

A keratolytic agent may be included as an active agent of a foamable composition. The term "keratolytically active agent" as used herein includes a compound that loosens and removes the stratum corneum of the skin, or alters the structure of the keratin layers of skin. Keratolytic active agents are used in the treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal, as well as adapalene, tazarotene, isotretinoin, acitretin and additional retinoids known in the art of pharmaceuticals and cosmetics are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another class of keratolytically active agents includes urea and urea derivatives.

Immunomodulators

In an embodiment, the active agent is an immunomodulator. Immunomodulators are chemically or biologically-derived agents that modify the immune response or the functioning of the immune system. Immunomodulators suitable for use according to the present invention include, among other options, cyclic peptides, such as cyclosporine, tacrolimus, tresperimus, pimecrolimus, sirolimus, verolimus, laflunimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated.

Retinoids

In an embodiment, the active agent is a retinoid. Retinoids suitable for use according to the present invention include, among other options, retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as any additional retinoids known in the art of pharmaceuticals and cosmetics; and analogs, derivatives, salts, ions and complexes thereof.

Anti-Acne and Anti-Rosacea Active Agents

In an embodiment, the active agent is an anti-acne or an anti-rosacea agent. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, coal tar, zinc salts and complexes, and combinations thereof, in a therapeutically effective concentration.

Antipsoriasis Agents

In an embodiment, the active agent is an anti-psoriasis agent. Such anti-psoriasis agents can be selected, among other options, from the group of keratolytically-active agents, salicylic acid, coal tar, anthralin, corticosteroids, vitamin D and derivatives and analogs thereof, including vitamin D3 analogs such as calcitriol, calcipotriol; retinoids, and photodymamic therapy agents.

Antiinfective Agents

In an embodiment, the active agent is an anti-infective agent. Such anti-infective agent can be selected from the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

The Foamable Composition Essential Ingredients as Active Agents

In certain embodiments, a hydrophobic solvent possesses therapeutic properties on its own and therefore, it can be regarded as "active agent." For example, some essential oils kill microorganisms and can be effective in the treatment or prevention of conditions that involve microbial infection, such as bacterial, fungal and viral conditions. Additionally, the occlusive effect of hydrophobic solvents is useful for the treatment of conditions which involve damaged skin, such as psoriasis or atopic dermatitis. The combination of a hydrophobic solvent and a therapeutically effective fatty alcohol or fatty acid may afford a synergistic beneficial effect in conditions characterized, for example, by infection and/or inflammation.

Combination of Active Agents

Several disorders involve a combination of more than one etiological factor; and therefore, the use of more that one active agents is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the foamable pharmaceutical composition can be desirable. Thus, in one or more embodiments, the foamable composition further includes at least two active agents, in a therapeutically effective concentration.

In an embodiment one of the active agents is a vitamin, a vitamin derivative or analogue thereof. In a preferred embodiment the vitamin, vitamin derivative or analogue thereof is oil soluble.

Microsponges

Microsponges (or microspheres) are rigid, porous and spongelike round microscopic particles of cross-linked polymer beads (e.g., polystyrene or copolymers thereof), each defining a substantially noncollapsible pore network. Microsponges can be loaded with an active ingredient and can provide a controlled time release of the active ingredient to skin or to a mucosal membrane upon application of the formulation. The slow release is intended to reduce irritation by the active ingredient. Microsponge® delivery technology was developed by Advanced Polymer Systems. In one or more embodiments the composition comprises one or more active agents loaded into Microponges with a waterless carrier described herein, which may also comprise a modulating agent.

Fields of Applications

The foamable carrier of the present disclosure is suitable for treating any inflicted surface. In one or more embodiments, foamable carrier is suitable for administration to the skin, a body surface, a body cavity or mucosal surface, e.g., the cavity and/or the mucosa of the nose, mouth, eye, respiratory system, vagina, urethra, rectum and the ear canal (severally and interchangeably termed herein "target site").

The foamable carrier of the present disclosure is also suitable for preventing a disorder or disease prior to its onset. The foamble carrier comprising for example a tetracycline may be applied to a body surface or a body cavity to try and prevent apoptosis, a disorder or disease prior to onset thereof. For example, prior to an anticipated inflammatory reaction or risk thereof, or prior to an anticipated onset of apoptosis or a risk thereof, or prior to an anticipated onset of inflammatory cytokines or risk thereof, prior to a medical procedure requiring intervention such as chemo therapy; radiotherapy, photodynamic therapy, laser therapy, etc. An simple example of prevention use, such as in the case of an eye infection say of one eye, is where the foam comprising a tetracycline (or the formulation prior to addition of propellant) is applied to the skin surface surrounding both eyes so as to reduce the risk of the infection spreading to the second eye or alternatively or additionally to the eye itself.

According to another embodiment a none limiting list of disorders where a tetracycline antibiotic might be used to prevent a disease or disorder is includes prophylaxis of gonococcal and chlamydial ophthalmia, neonatal conjunctivitis, periodontal disease, postoperative tetracycline, prophylaxis in pregnancy termination, for prevention of skin rash/acneiform skin eruption during cancer therapy, intraoperative topical tetracycline sclerotherapy following mastectomy for prevention of postoperative mastectomy seromas etc.

By selecting a suitable active agent, or a combination of at least two active agents, the foamable composition of the present disclosure is useful in treating an animal or a human patient having any one of a variety of dermatological diseases or disorders; in alleviating such diseases or disorders; or where such agent or agents have shown proficiency in preventative therapy in preventing such diseases or disorders, including but not limited to abscess, acne, acne conglobata, acne fulminans, acne vulgaris, acne scars, acute febrile neutrophilic dermatosis, acute lymphangitis, allergic contact dermatitis, alopecia, athlete's foot, atopic dermatitis, bacterial skin infections, baldness, basal cell carcinoma, blisters, bromhidrosis, bullous pemphigoid, burn, calluses candidiasis, carbuncles, cellulitis, chemical burns, chicken pox, cholesteatoma, cholinergic urticaria, chronic effects of sunlight, cold sores, cold urticaria, comedones, corns, creeping eruption, cutaneous abscess, cutaneous larva migrans, cutaneous myiasis, dark spots, delusional parasitosis, Dercum disease, dermatitis, dermatitis herpetiformis, dermatological pain, dermatological inflammation, dermographism, dermatophytoses, drug eruptions and reactions, dyshidrotic eczema, ectodermal dysplasia, eczema, ecthyma, epidermoid cyst, epidermal necrolysis, erysipelas, erysipelas, erythrasma, exfoliative dermatitis, erythema multiforme, erythema nodosum, folliculitis, fungal nail infections, fungal skin infections, furuncles, gangrene, genital herpes, granuloma annulare, head lice, hidradenitis suppurativa, hives, folliculitis, hirsutism, hyperhidrosis, hypohidrosis, ichthyosis, impetigo, inflammatory acne, ingrown nails, intertrigo, irritant contact dermatitis, ischemic necrosis, itching, jock itch, Kaposi's sarcoma, keratosis pilaris, lichen simplex chronicus, lichen planus, lichen sclerosus, lymphadenitis, lymphadenitis, lymphangitis, malignant melanoma, mastocytosis, measles, melanoma, melanoma, miliaria, moles, molluscum contagiosum, MRSA, necrotizing subcutaneous infection, necrotizing fasciitis, necrotizing myositis, nodular papulopustular acne, non-inflammatory acne, nummular dermatitis, oral herpes, panniculitis, parapsoriasis paronychia, parasitic skin infections, pemphigus, photoallergy, photo-damage, photo-irritation, photosensitivity, papules, pediculosis, perioral dermatitis, pimples, pityriasis rosea, pityriasis Lichenoides, pityriasis rosea, pityriasis rubra pilaris, poison ivy, poison oak post-operative or post-surgical skin conditions, pressure ulcers, pressure urticaria, pruritis, pseudofolliculitis barbae, psoriasis, PUPPP, purpura, pustules, pyogenic granuloma, rash, ringworm, rosacea, roseola, rubella, scabies, scalded skin syndrome, scarring, scleroderma, sebaceous cyst, seborrheic dermatitis, seborrheic keratosis, shingles, skin aging, skin cancer, skin neoplasia, skin neoplasms, skin rash, skin ulcers, squamous cell carcinoma, staphylococcal scalded skin syndrome, stasis dermatitis, Stevens-Johnson syndrome, sunburn, sun spots, thermal burns, tinea corporis, tinea cruris, tinea pedis, tinea versicolor, toxic epidermal necrolysis, trauma or injury to the skin, varicella zoster virus, vitamin D deficiency, viral skin infections, vitiligo, warts, water hives, wrinkles, xerosis, yeast skin infections and zoster.

Likewise, the foamable composition of the present disclosure is suitable for preventing or treating or alleviating a disorder of a body cavity or mucosal surface, e.g., the mucosa of the nose, mouth, eye, ear, respiratory system, vagina, urethra, or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present disclosure, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present disclosure, the composition is useful for the treatment of wound, ulcer and burn. This use is particularly important since the composition of the present disclosure creates a thin, semi-occlusive layer, which coats the damaged tissue, while allowing exudates to be released from the tissue.

The composition of the present disclosure is also suitable for administering a hormone to the skin or to a mucosal membrane or to a body cavity, in order to deliver the hormone into the tissue of the target organ, in any disorder that responds to treatment with a hormone.

In one embodiment the disorder is an inflammation, skin inflammation, acne, rosacea, actinic keratosis, skin cancer, a local pain, joint pain and osteoarthritis; the active agent is a nonsteroidal anti-inflammatory drug, given at a therapeutically effective concentration.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Cosmetic Use

In one or more embodiments, the composition may be used for cosmetic use. For example it may be used as part of a cosmetic formulation to prevent a cosmetic disorder or to improve the skin. Alternatively it may be used with cosmetic effect for example as a cosmetic remover. It can be dispensed in small quantities as a foam targeted to a surface and applied locally with mechanical force causing the foam to break.

Route of Administration

The formulations disclosed herein can be applied to the target site as a foam. In one or more alternative embodiments the formulations are prepared without propellant and are applied as a gel or ointment, for example, with the tetracycline as a suspension. Application can be hourly, 2 hourly, 3 hourly, four hourly, six hourly or eight hourly, twelve hourly, daily, alternate-day or intermittent, as necessary. For reasons of compliance less frequent applications, where possible are preferable such as twice-daily or daily single applications. In cases where prolonged or long term treatment is required a higher initial dose is provided followed by a gradual reduction to a lower maintenance dose, which can be increased if further outbreaks occur.

The formulations are suitable for administration directly or indirectly to an inflicted area, in need of treatment, through the following routes of administration:

1. Topical administration: for local effect, it is applied directly where its action is desired;
2. Enteral: when the desired effect is systemic (non-local), it is given via the digestive tract; and
3. Parenteral: when the desired effect is systemic, it is given by other routes than the digestive tract The following list more specifically exemplifies some routes of administration.

1. Topical

Topical administration is any form of administration that reaches a body organ topically, such as epicutaneous administration (application onto the skin), inhalation, enema, eye drops (onto the conjunctiva), ear drops, intranasal (into the nose) and vaginal.

Exemplary dosage forms that are suitable for topical administration of the stable tetracycline formulations include cream, gel, liniment, lotion, ointment, paste, spray, foam, mousse, lacquer (e.g., for nail treatment) and transdermal patch. Additionally, topical vaginal dosage forms may include a douche, an intrauterine device, a pessary (vaginal suppository), a vaginal ring and a vaginal tablet.

Rectal dosage forms include enema and suppositories. Inhaled dosage forms include aerosol inhalers, metered dose inhalers and solutions for nebulizer. Ophthalmic dosage forms include eye drop (solution or suspension), ophthalmic gel and ophthalmic ointment. In a preferred embodiment the dosage form is a foam that is thermally stable and breakable under shear force but is not "quick breaking" which allows comfortable application and well directed administration to the target area.

2. Enteral

Enteral is any form of administration that involves any part of the gastrointestinal tract by mouth (orally), as buccal or sublingual tablets, capsules, suspensions, solutions, powder or drops; by gastric feeding tube, duodenal feeding tube, or gastrostomy; and rectally, in suppository or enema form.

3. Parenteral by Injection or Infusion

Intravenous (into a vein); intraarterial (into an artery); intramuscular (into a muscle); intracardiac (into the heart); subcutaneous (under the skin); intraosseous infusion (into the bone marrow); intradermal, (into the skin itself); intrathecal (into the spinal canal); and intraperitoneal (into the peritoneum).

4. Other Parenteral

Transdermal (diffusion through the intact skin); transmucosal (diffusion through a mucous membrane), e.g. insufflation (snorting), sublingual, buccal (absorbed through cheek near gumline) and vaginal; and inhalational; epidural (synonym: peridural) (injection or infusion into the epidural space); and intravitreal.

EXAMPLES

The invention is described with reference to the following examples, in a non-limiting manner. The following examples exemplify the compositions and methods described herein. The examples are for the purposes of illustration only and are not intended to be limiting. Many variations will suggest themselves and are within the full intended scope.

Example 1—General Manufacturing Procedures

The following procedures are used to produce foam samples described in the examples below, in which only the steps relevant to each formulation are performed depending on the type and nature of ingredients used.

Step 1: Hydrophobic solvents are heated to 60-70° C.

Step 2: Waxes (and any fatty alcohols, if at all present, fatty acids, if at all present, or surfactants, if at all present) are added to the hydrophobic solvent and the formulation is mixed until complete melting.

Step 3: The formulation is cooled down to 30-40° C., active ingredients, if present, are added and the formulation is mixed until homogeneity is obtained.

Step 4: The formulation is cooled down to room temperature under mixing and packaged into suitable containers.

Materials

TABLE 1

Exemplary possible ingredients suitable for the production of foamable compositions disclosed herein. Equivalent materials from other manufacturers can also be used satisfactorily.

| Chemical Name | Function | Commercial Name | Supplier |
| --- | --- | --- | --- |
| Beeswax white | Foam adjuvant | Beeswax white | Henry Lamotte |
| Benzoyl Peroxide | Active agent | Benzoyl Peroxide | Spectrum |
| C12-15 Alkyl Benzoate | Solvent | C12-15 Alkyl Benzoate | Degussa |
| Calcitriol | Active agent | Calcitriol | Solvay Pharmaceutical |
| Capric/caprylic triglycerides | Solvent | Captex 355 | Abitec |
| Cyclomethicone-5 | Solvent | ST-cyclomethicone-5 | Dow |
| Heavy Mineral Oil | Solvent | Paraffin oil liquid heavy | Gadot |
| Hydrogenated castor oil | Foam adjuvant | Cutina HR | Cognis |
| Isopropyl myristate | Solvent | Isopropyl Myristate Ph. | Cognis |
| Isopropyl palmitate | Solvent | Isopropyl Palmitate | Cognis |
| Lidocaine | Active agent | Lidocaine | Sigma |
| Light Mineral Oil | Solvent | Pioner 2076P | Hansen & Rosenthal |
| Minocycline HCl | Active agent | Minocycline HCl | Hovione |
| Mometasone Furoate | Active agent | Mometasone Furoate | Sicor de Mexico |
| Octyldodecanol | Solvent | Eutanol G | Cognis |
| Paraffin wax 42-44 | Wax | Paraffin 42-44 | Merck |
| Paraffin wax 51-53 | Wax | Paraffin 51-53 | Merck |
| Paraffin wax 58-62 | Wax | Paraffin 58-62 | Merck |
| PPG 15 stearyl ether | Solvent | Arlamol E | Uniqema |
| Propane/Isobutane/Butane (20:78:2) | Propellant | A-46 | Aeropres |
| Propane/Isobutane/Butane (55:18:27) | Propellant | AP-70 | Aeropres |
| Tetrafluoroethane | Propellant | Dymel 134a | DuPont |

By way of non-limiting example, tests are briefly set out below as would be appreciated by a person of the art.

Collapse Time, which is a measure or indication of thermal stability, is examined by dispensing a given quantity of foam and photographing sequentially its appearance with time during incubation at 36° C. The collapse time result is defined as the time when the foam height reaches 50% of its initial height or if the foam has not yet reached 50% of its initial height after say 180 seconds then the collapse time is recorded as being >180 seconds. By way of illustration one foam may remain at 100% of its initial height for three minutes, a second foam may reach 90% of its initial height after three minutes, a third foam may reach 70% of its initial height after three minutes, and a fourth foam may reach 51% of its initial height after three minutes, nevertheless in each of these four cases the collapse time is recorded as >180 secs since for practical purposes for easy application by a patient to a target the majority of the foam remains intact for more than 180 secs. If the foam for example reaches 50% of its original height after say 100 seconds it would be recorded as having a collapse time of 100 seconds. It is useful for evaluating foam products, which maintain structural stability at skin temperature for at least 1 minute. Foams which are structurally stable on the skin for at least one minute are termed "short term stable" carriers or foams. A rough corollary of collapse time is drainage. If the collapse time is short the drainage is high. Each bubble is comprised of a liquid phase surrounding an air or gas phase. The liquid drains under the influence of gravitation force. When a bubble thins it ultimately collapses or joins with anther bubble. So foams with high drainage are inherently unstable. A further factor is expansion time. Some foams expand very rapidly whilst others expand quite slowly. Expansion time is a measure of how long a foam may take to reach its full expansion or lowest density. In some cases expansion and collapse can offset one another to some degree. So in one aspect, for example, whilst a foam is still expanding it has also begun to collapse. In another aspect, a thermolabile formulation that can collapse quite quickly in seconds upon expose to body temperature of about 36° C. may nevertheless have quite a relatively long expansion time at 20° C. In certain aspects the collapse time, expansion time and drainage time can all be long.

Density: in this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a pre-weighed tube, filling it until excess is extruded. Immediately remove (level off) excess foam at both ends and weigh the filled tube on the weighing balance.

Viscosity is measured with Brookfield LVDV-II+PRO with spindle SC4-25 at ambient temperature and 20, 10, 5 and or 1 RPM. Viscosity is usually measured at 10 RPM or 20 RPM. However, at about the apparent upper limit for the spindle of ~>50,000 CP, the viscosity at 1 RPM may be measured, although the figures are of a higher magnitude.

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

| Table of Shakability scoring | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Bubble Size: Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera is a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Chemical Stability: the amount of active agent present is analyzed chromatographically. Analysis is carried out after formulation preparation and at appropriate time intervals thereafter. The samples are typically stored in controlled temperature incubators at one or more of 5° C., 25° C. and 40° C. for several weeks or months. At appropriate time intervals samples are removed from the incubators and the concentration of active agent and or breakdown product is measured.

Example 2—Formulations Containing Waxes and Propellant or Oil and Propellant

The foaming properties of formulations containing waxes and propellant with no additional solvent were studied. Formulations were prepared containing Paraffin wax 51-53 and different concentrations of propellant. Also a formulation with mineral oil and propellant was prepared. As shown in Tables 2a and 2b below, upon addition of propellant, the formulations did not produce foam. It can be appreciated that the formulation of quality waterless foams based on waxes is challenging without the presence of foam stabilizers such as surfactants either alone or combined with foam adjuvants.

TABLE 2a

Formulations containing waxes and propellant

| Formulations | 001 | 002 | 003 |
|---|---|---|---|
| Ingredients | % w/w | % w/w | % w/w |
| Paraffin wax 51-53 | 100.0 | 100.0 | 100.0 |
| Total | 100.0 | 100.0 | 100.0 |
| Propellant AP-70 | 30.0 | 50.0 | 60.0 |
| Results | | | |
| Foam Quality | No Foam | No Foam | No Foam |

TABLE 2b

Formulation containing oil and propellant

| Formulations | XX2b |
|---|---|
| Ingredients | % w/w |
| Light mineral oil | 100.0 |
| Total | 100.0 |
| Propellant AP-70 | 10.0 |
| Results | |
| Foam Quality | Poor |

Comment: Neither Mineral Nor Paraffin Waxes Alone were Able to Generate a Foam.

Example 3—Mineral Oil-Based Formulations Containing Waxes

The foaming properties of mixtures of oils and waxes were studied. Formulations were prepared containing oils such as mineral oils and silicones in combination with waxes such as Paraffin wax 42-44, beeswax and hydrogenated castor oil were prepared, where the concentration of wax was from 10% to 20%. As shown in Table 3 below, upon addition of propellant, formulations 1-4 produced no more than bubbly liquids and formulations 8-10, although they were better, still only produced unstable fairly good quality foams that collapsed within seconds. It can be appreciated that the formulation of stable quality foams based on a combination of oils and waxes is challenging without the presence of foam stabilizers such as surfactants either alone or combined with foam adjuvants. Of all the formulations, paraffin wax and mineral oil achieved the poorest result. Without being bound by any theory the variations between paraffin waxes and their success in generating foams may be due to one or more factors such as chain length, van der Waals forces, and CST as explained above in the discussion.

TABLE 3

Mineral oil-based formulations containing waxes

| Formulations Ingredients | 004 % w/w | 005 % w/w | 006 % w/w | 007 % w/w | 008 % w/w | 009 % w/w | 010 % w/w |
|---|---|---|---|---|---|---|---|
| Heavy mineral oil | 80.0 | 60.0 | 80.0 | 60.0 | 60.0 | 85.0 | 85.0 |
| Light Mineral oil | — | 30.0 | — | 25.0 | 25.0 | — | — |
| Cyclomethicone | — | — | — | 5.00 | 5.00 | — | — |
| Paraffin wax 42-44 | 20.0 | — | — | — | — | — | — |
| Beeswax | — | 10.0 | 20.0 | 5.0 | — | — | — |
| Hydrogenated castor oil | — | — | — | 5.0 | 10.0 | 15.0 | 15.0 |
| Total | 100.0 | 100.0 | 100.0 | 100.0 | 100.0 | 100.0 | 100.0 |
| Propellant AP-70 | 8.0 | — | 8.0 | — | — | 8.0 | 12.0 |
| Propellant A-46 | — | 12.0 | — | 12.0 | 12.0 | — | — |
| Results |  |  |  |  |  |  |  |
| Foam Quality | Poor | Fair | Fair | Fair | Fairly Good | Fairly Good | Fairly Good |
| Collapse Time at 36° C. (sec) | — | — | — | — | 10 | — | — |

Example 4—Mineral Oil-Based Foam Formulations Containing 51-53 or 42-44 Paraffin Waxes The foaming properties of formulations containing mineral oil and a paraffin wax having a melting point of about 51-53° C. were studied. As shown in Table 4a, 4b and 4c below, formulations containing 5% paraffin wax 51-53° C. (and by extrapolation less than 5%) only produced bubbly liquids. 7.5% paraffin wax 51-53° C. only produced fairly good foam. Formulations containing 55% and 60% paraffin wax 51-53° C. (and by extrapolation more than 60%) did not produce foam and a semi-solid content was expelled even upon increasing the concentration of propellant to 12% and to 16%. However, formulations containing from 10% to 50% paraffin wax 51-53, successfully generated good to excellent quality foams having a collapse time of about 2 minutes or higher at 36° C. These results are surprising given the fact that no known foam stabilizing agent such as surfactants is present and that the phenomena is concentration dependent. Moreover, no foam adjuvant such as a fatty alcohol or fatty acid is needed, and formulations containing only waxes generated quality foams. For high amounts of waxes, the inclusion of higher amounts of propellant was found useful, for example, in order to improve the flowability of the formulation within the canister, as can be shown in by the shakability results. For example, a formulation containing 50% heavy mineral oil and 50% paraffin wax 51-53 was pressurized with 8% propellant or 12% propellant (See Table 4c). With 8% propellant, the composition was such that a block occurred with substantially no content being expelled through the canister valve. However, increasing the amount of propellant to 12% enabled quality foam to be expelled. Additionally, as can be seen from formulations 31-34 that increasing propellant from 8% to 12% also resulted in a similar increase in collapse time from about 80 secs to about 120 secs. Without being bound by any theory it may be that the propellant was successful in reducing the viscosity of the formulation and or wax in the valve. The physical properties of formulation 016 containing 20% paraffin wax 51-53 are presented in Table 4e.

Formulations were prepared, based on the combination of mineral oil with a paraffin wax having a melting point of about 42-44° C. Both in the case of light and heavy mineral oil, breakable foams of quality were obtained having a collapse time of more than 1 minute at 36° C. when 40% of paraffin wax 42-44 was used. Notably, the stability of the foams at 36° C. was improved by using higher amounts of propellant.

Formulations were prepared, based on the combination of mineral oil with a paraffin wax having a melting point of about 58-62° C. Breakable foams of quality having a density between 0.1 and 0.2 g/mL and a collapse time of more than 3 minute at 36° C. were obtained when 10% and 20% of paraffin wax 58-62 were used.

Table 4e indicates that the formulation can exist as three separate phases when left to stand, viz, oil, wax, and propellant but re-disperses on moderate shaking.

In one or more embodiments, there is provided a foamable formulation containing a mineral oil, a paraffin wax and a propellant, wherein the formulation provides upon dispensing a breakable foam of quality which exhibits a collapse time when placed on a surface at 36° C. (or between about 20° C. to 36° C.) of about or more than 1 minute. In one or more embodiments the collapse time is about or more than 1½ minutes; is about or more than 2 minutes; is about or more than 2½ minutes; or is about or more than 3 minutes.

TABLE 4a

Mineral oil-based foam formulations containing paraffin waxes

| Formulations Ingredients | 011 % w/w | 012 % w/w | 013 % w/w | 014 % w/w | 015 % w/w | 016 % w/w | 017 % w/w | 018 % w/w |
|---|---|---|---|---|---|---|---|---|
| Heavy mineral oil | 95.0 | 92.5 | 90.0 | 87.5 | 85.0 | 80.0 | 75.0 | 72.5 |
| Paraffin wax 51-53 | 5.0 | 7.5 | 10.0 | 12.5 | 15.0 | 20.0 | 25.0 | 27.5 |
| Total | 100.0 | 100.0 | 100.0 | 100.0 | 100.0 | 100.0 | 100.0 | 100.0 |
| Propellant AP-70 | 8.0 | 8.0 | 8.0 | 8.0 | 8.0 | 8.0 | 8.0 | 8.0 |
| Results | | | | | | | | |
| Foam Quality | Poor | Fairly Good | Good- | Good | Excellent | Excellent | Excellent | Excellent |
| Shakability | 2 | 2 | 2 | 2 | 2 | 2 | 1 | 1 |
| Collapse Time at 36° C. (sec) | — | — | 110 | 135 | >180 | >180 | >180 | >180 |

TABLE 4b

Mineral oil-based foam formulations containing paraffin waxes (cont.)

| Formulations Ingredients | 019 % w/w | 020 % w/w | 021 % w/w | 022 % w/w | 023 % w/w | 024 % w/w | 025 % w/w | 026 % w/w |
|---|---|---|---|---|---|---|---|---|
| Heavy mineral oil | 70 | 67.5 | 65.0 | 65.0 | 60.0 | 60.0 | 55.0 | 55.0 |
| Paraffin wax 51-53 | 30 | 32.5 | 35.0 | 35.0 | 40.0 | 40.0 | 45.0 | 45.0 |
| Total | 100.0 | 100.0 | 100.0 | 100.0 | 100.0 | 100.0 | 100.0 | 100.0 |
| Propellant AP-70 | 8.0 | 8.0 | 8.0 | 12.0 | 8.0 | 12.0 | 8.0 | 12.0 |
| Results | | | | | | | | |
| Foam Quality | Excellent | Excellent | Excellent | Excellent | Excellent | Excellent | Block | Excellent |
| Shakability | 1 | 1 | 1 | 2 | 0 | 1 | — | 0 |
| Collapse Time at 36° C. (sec) | >180 | >180 | >180 | >180 | >180 | >180 | — | >180 |

TABLE 4c

Mineral oil-based foam formulations containing paraffin waxes (cont.)

| Formulations Ingredients | 027 % w/w | 028 % w/w | XX4ca % w/w | XX4cb % w/w | 029 % w/w | 030 % w/w | 031 % w/w | 032 % w/w | 033 % w/w | 034 % w/w |
|---|---|---|---|---|---|---|---|---|---|---|
| Heavy mineral oil | 50.0 | 50.0 | 35.0 | 30.0 | — | — | 60.0 | 60.0 | — | — |
| Light Mineral oil | — | — | — | — | 60.0 | 60.0 | — | — | 60.0 | 60.0 |
| Paraffin wax 42-44 | — | — | — | — | — | — | 40.0 | 40.0 | 40.0 | 40.0 |
| Paraffin wax 51-53 | 50.0 | 50.0 | 55.0 | 60.0 | 40.0 | 40.0 | — | — | — | — |
| Total | 100.0 | 100.0 | 100.0 | 100.0 | 100.0 | 100.0 | 100.0 | 100.0 | 100.0 | 100.0 |
| Propellant AP-70 | 8.0 | 12.0 | 8 or 12 or 16.0 | 16.0 | 8.0 | 12.0 | 8.0 | 12.0 | 8.0 | 12.0 |
| Results | | | | | | | | | | |
| Foam Quality | Block | Excellent | No foam (semi-solid content expelled) | No foam (semi-solid content expelled) | Excellent | Excellent | Excellent | Excellent | Excellent | Excellent |
| Shakability | — | 0 | 1 | 1 | 1 | 2 | 1 | 2 | 1 | 2 |
| Collapse Time at 36° C. (sec) | — | >180 | — | — | >180 | >180 | 85 | 120 | 80 | 125 |

TABLE 4d

Mineral oil-based foam formulations containing paraffin waxes (cont.)

| Formulations | 035 | 036 | 037 | 038 |
|---|---|---|---|---|
| Ingredients | % w/w | % w/w | % w/w | % w/w |
| Heavy mineral oil | 90.0 | 80.0 | 80.0 | 70.0 |
| C12-C15 Alkyl benzoate | — | — | — | 10.0 |
| Paraffin wax 58-62 | 10.0 | 20.0 | 20.0 | 20.0 |

TABLE 4d-continued

Mineral oil-based foam formulations containing paraffin waxes (cont.)

| Formulations | 035 | 036 | 037 | 038 |
|---|---|---|---|---|
| Total |  |  |  |  |
| Propellant AP-70 | 8.0 | 8.0 | 12.0 | 12.0 |
| Results |  |  |  |  |
| Foam Quality | Excellent | Excellent | Excellent | Excellent |
| Foam Density (g/ml) | 0.135 | 0.119 | 0.129 | 0.177 |
| Shakability | 1 | 1 | 2 | 2 |
| Collapse Time at 36° C. (sec) | >180 | >180 | >180 | >180 |

TABLE 4e

Physical properties of formulation 016

| Formulations | 016 |
|---|---|
| Ingredients | % w/w |
| Heavy mineral oil | 80.0 |
| Paraffin wax 51-53 | 20.0 |
| Total |  |
| Propellant AP-70 | 8.0 |
| Results |  |
| Foam Quality | E |
| Shakability | 2 |
| Density (g/ml) | 0.230 |
| Collapse Time at 36° C. (sec) | >180 |
| Expansion time (sec) | 240 |
| Hardness (g) | 9 |
| Total dispensed weight (%) | 82.40 |
| Mean Bubble size (nm) | 259 |
| Inspection in Pressurized Glass bottle | 3 phases |
| PFF Centrifugation 3K rpm for 10 min | 3 phases |
| PFF Centrifugation 10K rpm for 10 min | 3 phases |
| PFF Viscosity at 10 rpm (cP) | 4303 |

The following example illustrates the physical stability of oleaginous foam formulation 016. In an accelerated stability study, samples were stored at 40° C., and parameters indicating physical stability such as foam quality, shakability, foam density and foam collapse time were determined. The stability test results following 1 and 2 months of storage at 40° C. are shown in Table 4f.

TABLE 4f

Physical properties of formulation 016 after 1 and 2 months at 40° C.

| Tests | T0 | 1 month at 40° C. | 2 months at 40° C. |
|---|---|---|---|
| Foam Quality | E | E | E |
| Shakability | Good | Poor-after vigorous shaking became good | Poor-after vigorous shaking moderate |
| Foam Density (g/ml) | 0.225 | 0.221 | 0.235 |
| Collapse Time at 36° C. (sec) | >180 | >180 | >180 |

Formulation 016 is physically stable after 2 months of storage at 40° C. The decrease in formulation shakability may be explained by a partial solidification of the wax content with time. It may be overcome inter alia by increasing the propellant concentration of the formulation to about 12%, or by using a propellant having a higher vapor pressure such as propane. So for example a smaller amount of higher pressure propellant may be used instead of a higher amount of a lower pressure propellant. In one or more embodiments the amount of propellant is at least about 11%; is at least about 12%; is at least about 13%; is at least about 14%; is at least about 15%; is at least about 16%; is at least about 17%; or is at least about 18%. In one or more embodiments the vapor pressure of the propellant is at least about 10 psi; is at least about 30 psi; is at least about 50 psi; is at least about 70 psi; is at least about 90 psi; is at least about 110 psi; is at least about 130 psi; or is at least about 150 psi. In one or more embodiments the vapor pressure of the propellant is between about 25 psi to about 125 psi. In one or more embodiments the vapor pressure of the propellant is between about 10 psi to about 130 psi. In one or more embodiments the vapor pressure of the propellant is between about 10 psi to about 30 psi; between about 25 psi to about 50 psi; between about 50 psi to about 70 psi; between about 70 psi to about 30 psi; between about 70 psi to about 90 psi; between about 90 psi to about 130 psi; between about 110 psi to about 130 psi; between about 30 psi to about 110 psi; between about 40 psi to about 90 psi.

Example 5—Foam Formulations Containing Waxes and Various Oils

The foaming properties of formulations containing various hydrophobic solvents and a paraffin wax having a melting point of about 51-53° C. were studied. As shown in Table 5 below, formulations containing oil such as capric/caprylic triglycerides, PPG-15 Stearyl ether, isopropyl palmitate, isopropyl myristate or octyldodecanol combined with 20% paraffin wax 51-53 produced breakable foams of quality having a collapse time of more than 1 minute at 36° C.

In one or more embodiments, there is provided a foamable formulation containing a hydrophobic solvent, a paraffin wax and a propellant, wherein the formulation provides upon dispensing a breakable foam of quality which exhibits a collapse time when placed on a surface at 36° C. (or between about 20° C. to 36° C.) of about or more than 1 minute. In one or more embodiments the collapse time is about or more than 1½ minutes; is about or more than 2 minutes; is about or more than 2½ minutes; is about or more than 3 minutes

TABLE 5

Foam formulations containing waxes and various oils

| Formulations | 039 | 040 | 041 | 042 | 043 |
|---|---|---|---|---|---|
| Ingredients | % w/w | % w/w | % w/w | % w/w | % w/w |
| Capric/caprylic triglycerides | 80.0 | — | — | — | — |
| PPG-15 Stearyl ether | — | 80.0 | — | — | — |
| Isopropyl palmitate | — | — | 80.0 | — | — |
| Isopropyl myristate | — | — | — | 80.0 | — |
| Octyldodecanol | — | — | — | — | 80.0 |
| Paraffin wax 51-53 | 20.0 | 20.0 | 20.0 | 20.0 | 20.0 |
| Total | 100.0 | 100.0 | 100.0 | 100.0 | 100.0 |
| Propellant AP-70 | 8.0 | 8.0 | 8.0 | 8.0 | 8.0 |
| Results |  |  |  |  |  |
| Foam Quality | Excellent | Excellent | Good | Good | Good |
| Shakability | 2 | 2 | 2 | 2 | 2 |
| Collapse Time at 36° C. (sec) | >180 | >180 | 180 | >180 | 165 |

Example 6—Foam Formulations Containing Oils, Waxes and Various Propellants

The foaming properties of formulations containing mineral oil, a paraffin wax and various types of propellants were studied. As shown in Table 6 below, formulations containing hydrocarbon propellants such as AP-70 and A-46, and hydrofluorocarbon propellants such as Dymel 134a produced breakable foams of quality having a collapse time of more than 1 minute at 36° C.

TABLE 6

Foam formulations containing oils, waxes and various propellants

| Formulations | 044 | 045 | 046 |
|---|---|---|---|
| Ingredients | % w/w | % w/w | % w/w |
| Heavy mineral oil | 80.0 | 80.0 | 80.0 |
| Paraffin wax 51-53 | 20.0 | 20.0 | 20.0 |
| Total | 100.0 | 100.0 | 100.0 |
| Propellant AP-70 (vapor pressure = 70 psi) | 8.0 | — | — |
| Propellant A-46 (vapor pressure = 46 psi) | — | 8.0 | — |
| Propellant Dymel 134a (vapor pressure = 96.6 psi) | — | — | 15.0 |

TABLE 6-continued

Foam formulations containing oils, waxes and various propellants

| Formulations | 044 | 045 | 046 |
|---|---|---|---|
| Results | | | |
| Foam Quality | Excellent | Good | Excellent |
| Shakability | 2 | 2 | 2 |
| Collapse Time at 36° C. (sec) | >180 | >180 | >180 |

Example 7—Foam Formulations Containing Oils, and Various Waxes

The foaming properties of formulations containing mineral oil, a propellant and other types of waxes were studied. As shown in Table 7 below, formulations containing solid waxes, namely about 20% hydrogenated castor oil, and formulations containing about 30% or about 40% beeswax produced breakable foams of quality having a collapse time of more than 1 minute at 36° C. For high amounts of waxes, the inclusion of higher amounts of propellant was found useful in order to improve the flowability of the formulation within the canister, as can be shown in by the shakability results.

In one or more embodiments, there is provided a foamable formulation containing a hydrophobic solvent, a wax and a propellant, wherein the formulation provides upon dispensing a breakable foam of quality which does not collapse at 36° C. for more than 1 minute.

TABLE 7

Foam formulations containing oils, waxes and other waxes

| Formulations | 047 | 048 | 049 | 050 | 051 | 052 |
|---|---|---|---|---|---|---|
| Ingredients | % w/w | % w/w | % w/w | % w/w | % w/w | % w/w |
| Heavy mineral oil | 80.0 | 80.0 | 60.0 | 60.0 | 70.0 | 70.0 |
| Beeswax | — | — | 40.0 | 40.0 | 30.0 | 30.0 |
| Hydrogenated castor oil | 20.0 | 20.0 | — | — | — | — |
| Total | 100.0 | 100.0 | 100.0 | 100.0 | 100.0 | 100.0 |
| Propellant AP-70 | 8.0 | 12.0 | 8.0 | 12.0 | 8.0 | 12.0 |
| Results | | | | | | |
| Foam Quality | Good | Good | Good | Excellent | Good | Good |
| Shakability | 0 | 0 | 0 | 1 | 1 | 2 |
| Collapse Time at 36° C. (sec) | — | >180 | — | >180 | >180 | >180 |

Example 8—Foam Formulations Containing Oils, Waxes and Various Active Ingredients The foaming properties of formulations containing mineral oil, a paraffin wax, a propellant and various active ingredients were studied. As shown in Table 8 below, formulations containing minocycline HCl, benzoyl peroxide (BPO), mometasone fuorate, calcitriol and lidocaine produced breakable foams of quality having a collapse time of more than 1 minute at 36° C. However, BPO and paraffin wax formed a block on repeated use.

TABLE 8

Foam formulations containing oils, waxes and various active ingredients

| Formulations | 053 | 054 | 055 | 056 | 057 |
|---|---|---|---|---|---|
| Ingredients | % w/w | % w/w | % w/w | % w/w | % w/w |
| Heavy mineral oil | 79.0 | 75.0 | 79.9 | 79.9985 | 75.0 |
| Paraffin 51-53 | 20.0 | 20.0 | 20.0 | 20.0 | 20.0 |
| Minocycline HCL | 1.0 | — | — | — | — |

TABLE 8-continued

Foam formulations containing oils, waxes and various active ingredients

| Formulations | 053 | 054 | 055 | 056 | 057 |
|---|---|---|---|---|---|
| Benzoyl peroxide | — | 5.0 | — | — | — |
| Mometasone furoate | — | — | 0.10 | — | — |
| Calcitriol | — | — | — | 0.0015 | — |
| Lidocaine | — | — | — | — | 5.0 |
| Total | 100.0 | 100.0 | 100.0 | 100.0 | 100.0 |
| Propellant AP-70 | 8.0 | 12.0 | 8.0 | 12.0 | 8.0 |
| Results | | | | | |
| Foam Quality | Excellent | Excellent | Excellent | Excellent | Excellent |
| Shakability | 2 | 2 | 2 | 2 | 2 |
| Collapse Time at 36° C. (sec) | >180 | Block | >180 | >180 | >180 |

Example 9—Compatibility Study

Procedure: Minocycline hydrochloride ("MCH") was incubated as a suspension with various excipients at 25° C. and 40° C. for maximum of sixty days or to the point where degradation was suspected. The ratio between MCH and the tested excipient is detailed below. Visual inspection was the major criterion for indication of compatibility. The color of intact MCH suspension is pale yellow; and any change of color (e.g., to dark orange, red, green, brown and black) indicates oxidation or degradation.

Hydrophilic solvents were tested for compatibility with MCH at a ratio of MCH: excipient of 1:250. Dimethyl Isosorbide, Glycerin, Ethanol, Propylene glycol, Butylene Glycol, PEG 200, Hexylene Glycol, PEG 400, Dimethyl Sulfoxide and Diethylene glycol monoethyl ether were found to be incompatible with MCH.

Oily emollients and waxes were tested for compatibility with MCH at a ratio of MCH: excipient of 1:250 for Oily emollients and 1:50 for waxes. Hydrogenated castor oil, Castor oil, Cocoglycerides, Disopropyl adipate, Mineral oil light, Coconut oil, Beeswax, MCT oil, Cyclomethicone, Isododecane, Cetearyl octanoate, Gelled mineral oil, Isopropyl myristate, PPG 15 stearyl ether, Mineral oil heavy, Octyl dodecanol, White Petrolatum, Petrolatum (Sofmetic), Paraffin 51-53, Calendula oil, Shea butter, Grape seed oil, Almond oil, Jojoba oil, Avocado oil, Peanut oil, Wheat germ oil and Hard Fat were found to be compatible with MCH. Pomegranate seed oil was found to be incompatible with MCH.

The compatibility of MCH with hydrophobic surfactant was tested following solubilization of the surfactant in mineral oil (mineral oil was previously shown to be compatible with MCH). Surfactants were tested for compatibility with MCH at a ratio of MCH: excipient of 1:50. PEG150 distearate, Laureth 4, PEG 40 hydrogenated castor oil, PEG 75 lanolin, Glucam P20 distearate, PEG100 stearate, Glyceryl monostearate, PEG 40 stearate, Montanov S (Cocoyl Alcohol (and) C12-20 Alkyl Glucoside)), Alkyl lactate, Benton gel, SPAN 60, Sorbitan sesquistearate, SPAN 40, Tween 20, Ceteth 2, Sucrose stearic acid esters D1813, Ceteareth 20, Steareth 2/Steareth 21, Methyl glucose sesquistearate, Oleth 20, PPG 20 methyl glucose ether, Tween 60 were found to be incompatible with MCH. Sucrose stearic acid esters D1803, Sucrose stearic acid esters D1807 and Sucrose stearic acid esters D1811 were found to be compatible with MCH; however, not all of them dissolved in oil (e.g. 1811, 1813).

Foam adjuvants were tested for compatibility with MCH at a ratio of MCH: excipient of 1:50. Isostearyl alcohol, Behenyl alcohol, Stearyl alcohol, Cetyl alcohol, Oleyl alcohol, Myristyl alcohol, Cetostearyl alcohol, Palmitic acid, Stearic acid and Oleic acid were found to be compatible with MCH. Isostearic acid was not compatible with MCH.

Additives were tested for compatibility with MCH at a ratio of MCH: excipient of 1:50. Aerosil and Menthol were found to be compatible with MCH. Titanium dioxide and Ethocel were not compatible with MCH.

Additives were tested for compatibility with MCH. Minimal quantities of water (1004) were added to MCH, suspended in excipients that had demonstrated compatibility to examine whether water can enhance oxidation/degradation in the absence or presence of antioxidant. In parallel, antioxidants were added to the MCH suspensions comprising water. Antioxidants were also added to excipients which were found to be non compatible with MCH. Addition of water caused prompt degradation of MCH. Addition of the antioxidants alpha-tocopherol, BHA/BHT and propyl gallate did not prevent MCH degradation. Compatible excipients became incompatible in the presence of water. Addition of antioxidants did not alter this result.

What is claimed is:

1. A method of treating acne vulgaris or rosacea, comprising administering a waterless foam composition free of surfactant and polymeric agent comprising
   a tetracycline antibiotic and a foamable carrier,
   the foamable carrier comprising:
   a) about 50% to about 90% by weight of the foamable carrier of a liquid oil and about 10% to about 50% by weight of the foamable carrier of a paraffin wax selected from the group consisting of a paraffin wax having a melting point of 58-62° C., a paraffin wax having a melting point of 51-53° C. and a mixture thereof, wherein the total weight of the liquid oil and wax together is between about 85% and about 100% by weight of the foamable carrier; or
   b) about 40% by weight of the foamable carrier of a liquid oil and about 60% by weight of the foamable carrier of a paraffin wax having a melting point of 42-44 c'C; and
   a liquefied or compressed gas propellant; and
      wherein the ratio of the foamable carrier to the propellant is from about 100:4 to about 100:25; and
      wherein the composition is substantially free of a foam adjuvant.

2. The method of claim 1, wherein the administered foam composition further comprises a second active agent.

3. The method of claim 1, wherein the foamable carrier further comprises a second wax that has a melting point between about 47° C. and about 64° C. or wherein the second wax is selected from a hydrogenated castor oil, a beeswax, and a mixture thereof.

4. The method of claim 2, wherein the second active agent is selected from the group consisting of an active herbal extract, an acaricide, an age spot and keratose removing agent, an allergen, an alpha hydroxyl acid, an analgesic agent, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic agent, an antifungal agent, an antihistamine, an antihelminth agent, an antihyperkeratolyte agent, an anti-infective agent, an anti-inflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an antiyeast agent, an astringent, a beta-hydroxy acid, benzoyl peroxide, a topical cardiovascular agent, a chemotherapeutic agent, a corticosteroid, an immunogenic substance, a dicarboxylic acid, a disinfectant, a fungicide, a hair growth regulator, a haptene, a hormone, a hydroxy acid, an immunosuppressant, an immunoregulating agent, an immunomodulator, an insecticide, an insect repellent, a keratolytic agent, a lactam, a local anesthetic agent, a lubricating agent, a masking agent, a metals, a metal oxide, a mitocide, a neuropeptide, a non-steroidal anti-inflammatory agent, an oxidizing agent, a pediculicide, a peptide, a protein, a photodynamic therapy agent, a radical scavenger, a refatting agent, a retinoid, a sanative, a scabicide, a self tanning agent, a skin protective agent, a skin whitening agent, a steroid, a steroid hormone, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover, an androgen, an anti-hyperkeratosis agent, an estrogen, an immunestimulant, a pesticide, a progesterone, a sedative, a vaso active agent, and a mixture of any two or more thereof.

5. The method of claim 1, wherein the tetracycline antibiotic is a minocycline or a doxycycline.

6. The method of claim 2, wherein the second active agent is a retinoid.

7. The method of claim 1, wherein the foamable carrier further comprises about 1% or less than 1% by weight of the foamable carrier of a foam adjuvant.

8. The method of claim 1, wherein the composition is free of foam adjuvant.

9. The method of claim 1, wherein the foamable carrier further comprises about 5% or less than 5% by weight of the foamable carrier of polyols.

10. The method of claim 1, wherein the composition is free of short chain alcohols.

11. The method of claim 1, further comprising a solid or semi-solid oil.

12. The method of claim 1, wherein the composition is free of short chain alcohol and polyol.

* * * * *

UNITED STATES PATENT AND TRADEMARK OFFICE
CERTIFICATE OF CORRECTION

PATENT NO. : 10,967,063 B2  
APPLICATION NO. : 16/019623  
DATED : April 6, 2021  
INVENTOR(S) : Dov Tamarkin et al.

Page 1 of 1

It is certified that error appears in the above-identified patent and that said Letters Patent is hereby corrected as shown below:

On the Title Page

Item (54) and in the Specification, Column 1, Line 2 of title, "FORMABLE COMPOSITION AND" should read --FOAMABLE COMPOSITION AND--.

In the Claims

Claim 1, Column 60, Line 57, "42-44 c'C;" should read --42-44° C.;--.

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*